US009476871B2

(12) United States Patent
Perree et al.

(10) Patent No.: US 9,476,871 B2
(45) Date of Patent: Oct. 25, 2016

(54) SYSTEM AND METHOD FOR AUTOMATED DETERMINATION OF THE RELATIVE EFFECTIVENESS OF ANTI-CANCER DRUG CANDIDATES

(71) Applicant: DiaTech Oncology LLC, Franklin, TN (US)

(72) Inventors: Mathieu Perree, Montreal (CA); Allan E. Hallquist, Morning View, KY (US); Olivier Petit, Montreal (CA)

(73) Assignee: DiaTech Oncology LLC, Franklin, TN (US)

( * ) Notice: Subject to any disclaimer, the term of this patent is extended or adjusted under 35 U.S.C. 154(b) by 371 days.

(21) Appl. No.: 13/803,623

(22) Filed: Mar. 14, 2013

(65) Prior Publication Data
US 2014/0141462 A1 May 22, 2014

Related U.S. Application Data

(60) Provisional application No. 61/641,610, filed on May 2, 2012.

(51) Int. Cl.
*G06F 19/20* (2011.01)
*G01N 33/50* (2006.01)
*G06F 19/00* (2011.01)

(52) U.S. Cl.
CPC ......... *G01N 33/5044* (2013.01); *G06F 19/709* (2013.01); *G06F 19/704* (2013.01)

(58) Field of Classification Search
CPC ................................ G06F 19/00; G06F 33/00
USPC ........................................................ 702/19, 20
See application file for complete search history.

(56) References Cited

U.S. PATENT DOCUMENTS

| 5,356,793 A | 10/1994 | Koezuka et al. |
| 6,077,684 A | 6/2000 | Kravtsov |

(Continued)

FOREIGN PATENT DOCUMENTS

| KR | 100721927 B1 | 5/2007 |
| WO | WO-02/46751 A2 | 6/2002 |

OTHER PUBLICATIONS

Kraystov, et al.; "Use of the Microculture Kinetic Assays of Apoptosis to Determine Chemosensitivities of Leukemias"; Blood, vol. 92, No. 3; pp. 968-980.
Ballard et al. (2010) "Endometrial carcinoma in vitro chemosensitivity testing of single and combination chemotherapy regimens using the novel microculture kinetic apoptosis assay; implications for endometrial cancer treatment," *Journal of Gynecologic Oncology*, 20(1):45-49.

(Continued)

*Primary Examiner* — Mary Zeman
(74) *Attorney, Agent, or Firm* — Goodwin Procter LLP

(57) ABSTRACT

A computer system is provided for determining the relative effectiveness of anti-cancer drugs. The interface has selectable options, including an option to manage drug testing parameters, and enables user selection of desired drug testing parameters in relation to a virtual well plate associated with a physical well plate of a spectrophotometer. The computer system causes the spectrophotometer to start a drug test, wherein the physical well plate includes at least one test well containing viable cancer cells; and at least one drug candidate in a predetermined concentration; and at least one control well containing the viable cancer cells alone. The system records the optical density of the well at a predetermined wavelength at selected time intervals for a selected duration of time, and stores the optical density and time measurements in the database. An activity value is calculated from the optical density and time measurements, and a correlation is displayed between the activity value and the drug candidate's ability to induce apoptosis in the cancer cells.

30 Claims, 47 Drawing Sheets

(56) References Cited

U.S. PATENT DOCUMENTS

| | | |
|---|---|---|
| 6,258,553 B1 | 7/2001 | Kravtsov |
| 6,448,030 B1 | 9/2002 | Rust et al. |
| 2005/0118600 A1 | 6/2005 | Aoki et al. |
| 2009/0221436 A1 | 9/2009 | Slanetz |
| 2010/0042351 A1 | 2/2010 | Covey et al. |
| 2011/0189693 A1 | 8/2011 | Choi et al. |
| 2011/0244503 A1* | 10/2011 | Perree et al. .................. 435/29 |
| 2012/0089341 A1 | 4/2012 | Roder et al. |
| 2012/0224053 A1* | 9/2012 | Vykoukal .......... B01L 3/502715 348/135 |
| 2013/0078733 A1* | 3/2013 | Holmes ................ B01L 3/0217 436/174 |
| 2015/0160193 A1 | 6/2015 | Presant et al. |

OTHER PUBLICATIONS

"SoftMax Pro Software Version 5 for Mac and Windows User Guide," (2009) https://us.vwr.com/store/asset?assetURI=https://us.vwr.com/stibo/hi_res/std.lang.all/95/51/6819551.pdf (193 pages).

International Search Report in International Application No. PCT/US2013/039189, mailed Sep. 13, 2013 (3 pages).

Written Opinion of the International Searching Authority in International Application No. PCT/US2013/039189, mailed Sep. 13, 2013 (5 pages).

Extended European Search Report in European Application No. 13784507.9 (based on International Patent Application No. PCT/US2013/039189), Dec. 3, 2015 (7 pages).

* cited by examiner

FIG. 17

| Read # | OD | VMax | Ctrl Slp | KU |
|---|---|---|---|---|
| 141 | 0.097 | 0.022 | 0.006 | 0.703 |
| 142 | 0.097 | 0.024 | 0.005 | 0.791 |
| 143 | 0.098 | 0.024 | 0.006 | 0.791 |
| 144 | 0.097 | 0.024 | 0.004 | 0.878 |
| 145 | 0.098 | 0.024 | 0.004 | 0.878 |
| 146 | 0.098 | 0.024 | 0.002 | 0.966 |
| 147 | 0.098 | 0.024 | 0.004 | 0.878 |
| 148 | 0.098 | 0.022 | 0.004 | 0.791 |
| 149 | 0.098 | 0.024 | 0.006 | 0.791 |
| 150 | 0.099 | 0.026 | 0.006 | 0.878 |
| 151 | 0.099 | 0.028 | 0.007 | 0.922 |
| 152 | 0.099 | 0.028 | 0.009 | 0.834 |
| 153 | 0.099 | 0.028 | 0.007 | 0.922 |
| 154 | 0.099 | 0.03 | 0.007 | 1.01 |
| 155 | 0.1 | 0.033 | 0.006 | 1.186 |
| 156 | 0.101 | 0.035 | 0.007 | 1.23 |
| 157 | 0.101 | 0.037 | 0.006 | 1.362 |
| 158 | 0.101 | 0.035 | 0.006 | 1.274 |
| 159 | 0.101 | 0.035 | 0.004 | 1.362 |
| 160 | 0.101 | 0.033 | 0.004 | 1.274 |
| 161 | 0.101 | 0.033 | 0.004 | 1.274 |
| 162 | 0.101 | 0.037 | 0.007 | 1.318 |
| 163 | 0.102 | 0.039 | 0.007 | 1.405 |
| 164 | 0.102 | 0.041 | 0.007 | 1.493 |
| 165 | 0.102 | 0.041 | 0.006 | 1.537 |
| 166 | 0.103 | 0.043 | 0.006 | 1.625 |
| 168 | 0.103 | 0.043 | 0.006 | 1.625 |
| 169 | 0.103 | 0.041 | 0.006 | 1.537 |
| 170 | 0.103 | 0.039 | 0.006 | 1.449 |
| 171 | 0.103 | 0.039 | 0.006 | 1.449 |
| 172 | 0.103 | 0.037 | 0.006 | 1.362 |
| 173 | 0.103 | 0.039 | 0.006 | 1.449 |
| 174 | 0.104 | 0.039 | 0.006 | 1.449 |

Well : C7

| _Templates |
|---|
| wellposition |
| name |
| drug1 |
| drug2 |
| drug3 |
| concentration1 |
| concentration2 |
| concentration3 |
| sample |
| colorcode |

| _TemplateCategory |
|---|
| category |

| _SerieDisplay |
|---|
| ReportID |
| Addendum |
| name |
| shape |
| color |
| size |
| visible |
| legend |

| _Physician |
|---|
| ⚷ name |
| phone |
| fax |
| hospital |

| _DrugConcentration |
|---|
| drugName |
| concentration |

| _Drugs |
|---|
| drugName |
| fullName |

| _ReportTemplates |
|---|
| templateName |
| type |
| text |

| _DrugCategoriesComp |
|---|
| reportID |
| categorie |
| drug1 |
| drug2 |
| difference |

*FIG. 47*
*(Cont'd)*

| _deletedData |
| --- |
| F16 |
| F17 |
| F18 |
| F19 |
| F20 |
| F21 |
| F22 |
| F23 |
| F24 |
| G1 |
| G2 |
| G3 |
| G4 |
| G5 |
| G6 |
| G7 |
| G8 |
| G9 |
| G10 |
| G11 |
| G12 |
| G13 |
| G14 |
| G15 |
| G16 |
| G17 |
| G18 |
| G19 |
| G20 |
| G21 |
| G22 |

| _DeletedTracking |
| --- |
| ⚷ trackingNumber |
| hospital |
| physician |
| contact |
| email |
| phone |
| civicNumber |
| street |
| city |
| state |
| zipCode |
| country |
| mediaPeremptionDate |
| kitType |
| shippingDate |
| receivedDate |
| receivedLocation |

*FIG. 47*
*(Cont'd)*

SYSTEM AND METHOD FOR AUTOMATED DETERMINATION OF THE RELATIVE EFFECTIVENESS OF ANTI-CANCER DRUG CANDIDATES

CROSS-REFERENCE TO RELATED APPLICATIONS

This nonprovisional application claims the benefit of priority to provisional application U.S. Ser. No. 61/641,610, filed on May 2, 2012.

STATEMENT REGARDING FEDERALLY SPONSORED RESEARCH OR DEVELOPMENT

Not applicable.

THE NAMES OF THE PARTIES TO A JOINT RESEARCH AGREEMENT

Not applicable.

BACKGROUND OF THE INVENTION

1. Field of the Invention

The present invention relates to systems and methods used to determine the relative effectiveness of anti-cancer drugs on live cells from tissue, blood, and fluids, and more particularly to such systems and methods employing spectrophotometry to assess optical density of cells in response to treatments employing anti-cancer drugs.

2. Description of Related Art

Cell death may occur in a variety of manners, but successful anti-cancer drugs tend to cause death of cancer cells by the very specific process of apoptosis. Apoptosis is a mechanism by which a cell disassembles and packages itself for orderly disposal by the body. Apoptosis is commonly used by the body to discard cells when they are no longer needed, are too old, or have become damaged or diseased. In fact, some cells with dangerous mutations that might lead to cancer and even some early-stage cancerous cells may undergo apoptosis as a result of natural processes.

During apoptosis, the cell cuts and stores DNA, condenses the nucleus, discards excess water, and undergoes various changes to the cell membrane, such as blebbing, the formation of irregular bulges in the cell membrane. Apoptosis generally occurs after one of several triggers sends a signal to the cell that it should undergo apoptosis. In many cancer cells, this message system does not work correctly because the cell cannot detect the trigger, fails to send a signal properly after the trigger is received, or fails to act on the signal, or the cell may even have combinations of these problems. The overall effect is a resistance to undergoing apoptosis in some cancer cells.

Cancer, as used herein, includes epithelial malignancies, leukemia, lymphomas and mesenchymal malignancies. Many effective cancer drugs can induce a cancer cell to undergo apoptosis despite its resistance to the process. Accordingly, there is a need to detect whether a particular drug candidate can cause apoptosis in various types of cancer cells and also to determine the drug candidate's effectiveness as compared to other drugs or drug candidates. A complete analysis of effectiveness depends heavily upon automated processes for communicating with spectrophotometric equipment employed in the techniques, as well as appropriate data processing and display to users and others involved in the decision-making process of determining which drug is most suitable.

The MiCK assay, described in U.S. Pat. No. 6,077,684 and U.S. Pat. No. 6,258,553 is currently used to detect whether cancer cells from a patient undergo apoptosis in response to a particular drug known to be effective against one or more types of cancer. In the MiCK assay cancer cells from a patient are placed in a suspension of a given concentration of single cells or small cell clusters and allowed to adjust to conditions in multiple wells of a microtiter plate. Control solutions or solutions with various concentrations of known anti-cancer drugs, typically those drugs recommended for the patient's cancer type, are introduced into the wells with one test sample per well. The optical density of each well is then measured periodically, typically every few minutes, for a period of typically a few days. As a cell undergoes apoptosis-related blebbing, its optical density increases in a nearly linear fashion. If the cell does not undergo apoptosis or dies from other causes, its optical density does not change in this manner. Thus, if a plot of optical density (OD) v. time for a well yields a straight line curve having a positive slope over the time interval, then the anti-cancer drug in that well induces apoptosis of the patient's cancer cells and might be a suitable therapy for that patient. OD v. time data may also be used to calculate kinetic units, which similarly correlate with the suitability of a therapy for the patient.

The applicants also have a pending U.S. patent application related to the underlying technology, U.S. Publication No. 2011/0244503, as well as an international patent application, PCT/US2010/029318, whose entire disclosures are incorporated herein by reference.

In view of the benefits of the MiCK assay and its evolving technologies to patients, healthcare providers, and other participants in the oncology field, what is needed is a system and method for automating the determination of the relative effectiveness of anti-cancer drug candidates. As described below, these tests and their associated parameters, inventory control, recording keeping, shipment tracking, and communication with various persons can become a tedious and time-consuming affair. Therefore, as these techniques become more widely used, it is critical that most aspects of the process are automated using modern computer systems and software so the quick and accurate results can be analyzed and disseminated accordingly.

SUMMARY OF THE INVENTION

A computer system for determining the relative effectiveness of anti-cancer drugs is provided, comprising a processor, the processor being a hardware component of the computer system; and a memory in communication with the processor, the memory storing a plurality of instructions that when executed by the processor, execute the steps of: (a) providing an interface application, displayed on an electronic device, said interface having selectable options including at least an option to manage drug testing parameters; (b) in response to a user selection, via an electronic input device, of the option to manage drug testing parameters, selecting desired drug testing parameters in relation to a virtual well plate associated with a physical well plate of a spectrophotometer in electronic communication with the processor, and storing the drug testing parameters in a database; (c) in response to a user selection, via an electronic input device, causing the spectrophotometer to start a drug test, wherein the physical well plate includes at least one test well containing: (1) viable cancer cells; and (2) at least one drug candidate in a predetermined concentration; and at least one control well containing the viable cancer cells alone; (d) recording the optical density of the well at a predetermined wavelength at selected time intervals for a selected duration of time, and storing the optical density and time measurements in the database; (e) calculating an activity value from the optical density and time measurements; and (f) displaying a correlation between the activity value and the drug candidate's ability to induce apoptosis in the cancer cells.

In a preferred embodiment, the activity value is a kinetic units value calculated based on changes in the optical density as a function of time caused by cell apoptosis.

In another embodiment, the interface further includes at least one option to manage drug testing projects, at least one option to manage patients whose cancer cells are tested, and at least one option to manage administrative tasks associated with the drug tests.

The database preferably resides on a server accessed by one or more workstations, and the server includes one or more services in communication with one or more spectrophotometers.

The system may further include an electronic alarm in communication with the database, wherein the alarm sends a notification to a designated recipient upon detection of an anomaly in optical density data being stored to the database.

The system may further include a remote power switch in communication with the server enabling remote power cycling of the spectrophotometer, a battery in operable communication with the remote power switch, and a generator capable of charging the battery.

Preferably, the interface includes a least one option to generate one or more reports based on the correlation between the activity value and the drug candidate's ability to induce apoptosis in the cancer cells. In a more preferred embodiment, the report includes comparative data between a plurality of drug candidates tested. In yet another embodiment, the report includes a list of the drug candidates tested in order of their respective activity value. In another embodiment, the report includes a comparative chart correlating the activity value of the drug candidates tested against one or more concentrations of the drug candidates tested.

The interface further preferably includes at least one option to manage cell lines used in connection with the drug tests.

A computer readable medium and methods in accordance with the present invention are also provided.

BRIEF DESCRIPTION OF THE DRAWINGS

FIGS. 11-46 depict various screen images of an automated application in accordance with the present invention.

Figure 1:
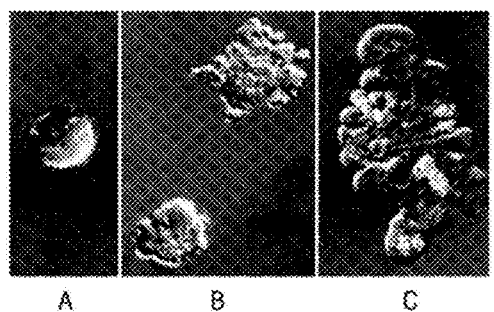
FIG. 1 shows a prior art photomicrograph of a cell. Part A of FIG. 1 shows the cell prior to apoptosis. Part B of FIG. 1 shows the cell during apoptosis when blebbing is occurring. Part C of FIG. 1 shows a cell when apoptosis is complete or nearly complete.

Appendices A, B, and C are sample reports which are generated by the automated application of the present invention.

DETAILED DESCRIPTION OF THE INVENTION

Prior to a description of the present invention, it is helpful to understand the underlying processes by which anti-cancer drug candidates are tested using the MiCK assay techniques mentioned above. The process relates to evaluation of anti-cancer drug candidates' effectiveness in causing apoptosis in cancer cells using a spectrophotometric assay to measure optical density (OD) over a period of time.

Assay

The assay may proceed by selecting an anti-cancer drug candidate and selecting at least one known cancer cell type on which to test the drug. The cancer cells may be suspended as a single-cell suspension in culture medium, such as RPMI. As used herein, a "single cell suspension" is a suspension of one or more cells in a liquid in which the cells are separated as individuals or in small clumps of 50 cells or fewer. The culture medium may contain other components, such as fetal-bovine serum or components specifically required by the cancer cells. These components may be limited to those necessary to sustain the cells for the duration of the assay, typically at least 24 hours and not longer than 120 hours.

Suspended cells may be tested by placing samples in wells of a spectrophotometric plate. The cells may be suspended at any concentration such that during the spectrophotometric measurements of OD, the beam of the plate reader normally passes through the layer of cells. For most cells a concentration of between $2\times10^5$ and $1\times10^6$ cells/mL may be used. Concentration may be increased for small cells and decreased for large cells. To more precisely determine the appropriate cell concentration, the volume of cell suspension to be used in drug candidate test samples may be added to at least one concentration test well of the plate. If the well will be prefilled with additional medium during testing of the drug candidates, then the concentration test well may similarly be prefilled with additional medium. After the concentration test well is filled, the plate may be centrifuged (e.g. for 30 seconds to 2 min at 500 RPM, depending on the plate type) to settle the cells on the bottom of the well. If the cell concentration is appropriate for the assay, the cells should form a monolayer without overlapping. Cell concentration may be adjusted as appropriate until this result is achieved. Multiple concentrations of cells may be tested at one time using different concentration test wells.

According to embodiments where the cells may grow significantly overnight or during another period of time between placement of the cells in the plate and commencement of the drug candidate assay, the cell concentration may be adjusted to initially achieve less than a monolayer to allow for growth such that sufficient cells for a monolayer will be present when the drug candidate assay commences.

The cancer cells may be in an exponential or a non-exponential growth phase. In a specific embodiment, particularly when the cancer cells are from a cancer cell line they may be in an exponential growth phase.

After the appropriate cell concentration has been determined, the drug-candidate assay may proceed by filling test and control wells in the plate with an appropriate volume of medium and an appropriate number of cells. In other embodiments the well may be partially pre-filled with medium alone.

After filling, the cells may be allowed to adjust to the plate conditions for a set period of time, such as at least 12 hours, at least 16 hours, at least 24 hours, or 12-16 hours, 12-24 hours, or 16-24 hours. An adjustment period may be omitted for non-adherent cells. The adjustment period is typically short enough such that the cells do not experience significant growth during the time. The adjustment period may vary depending on the type of cancer cells used in the drug candidate assay. Adjustment may take place under conditions suitable to keep the cells alive and healthy. For example, the plate may be placed in a humidified incubator at 37° C. under 5% $CO_2$ atmosphere. For some cell types, particularly cell types that do not undergo an adjustment period, such as leukemia or lymphoma cell lines, the plate may be centrifuged (e.g. for 30 seconds to 2 minutes at 500 RPM, depending on the plate type) to settle the cells on the bottom of the wells.

The drug candidate and any control drugs or other control samples may be added to the wells after the adjustment period. Typically the drug candidate will be added in a small volume of medium or other liquid as compared to the total volume of liquid in the well. For example, the volume of drug added may be less than 10% of the total volume of liquid in the well, although other percentage concentrations may be used to suit the particular needs of the situation. Drug candidates may be added in multiple dilutions to allow determination of any concentration effects. Although many drug candidates may be water-soluble, drug candidates that are not readily soluble in water may also be tested. Such candidates may be mixed with any appropriate carrier. Such candidates may preferably be mixed with carriers anticipated for actual clinical use. Viscous drug candidates may require substantial dilution in order to be tested. Drug candidates with a strong color may benefit from monitoring of OD in test wells containing only the drug candidate and subtraction of this OD from measurements for the test sample wells.

After addition of the drug candidate, the cells may be allowed another short period of adjustment, for example of 15 minutes or 30 minutes. The cells may be placed under conditions suitable to keep the cells alive and healthy. For example, the plate may be placed in a humidified incubator at 37° C. under 5% $CO_2$ atmosphere. After this short adjustment period, a layer of mineral oil may be placed on top of each well to maintain $CO_2$ in the medium.

The plate may then be placed in a spectrophotometer configured to measure the OD at a wavelength of 600 nm for each well at a given time interval for a given total period of time. For example, OD for each well may be measured periodically over a time frame of seconds, minutes, or hours for a period of between 24 and 120 hours. For certain cells measurements for a period of as little as 12 hours may be sufficient. In specific embodiments, measurements may be taken every 5 to 10 minutes. The spectrophotometer may have an incubated chamber to avoid spontaneous death of the cells.

Figure 2:
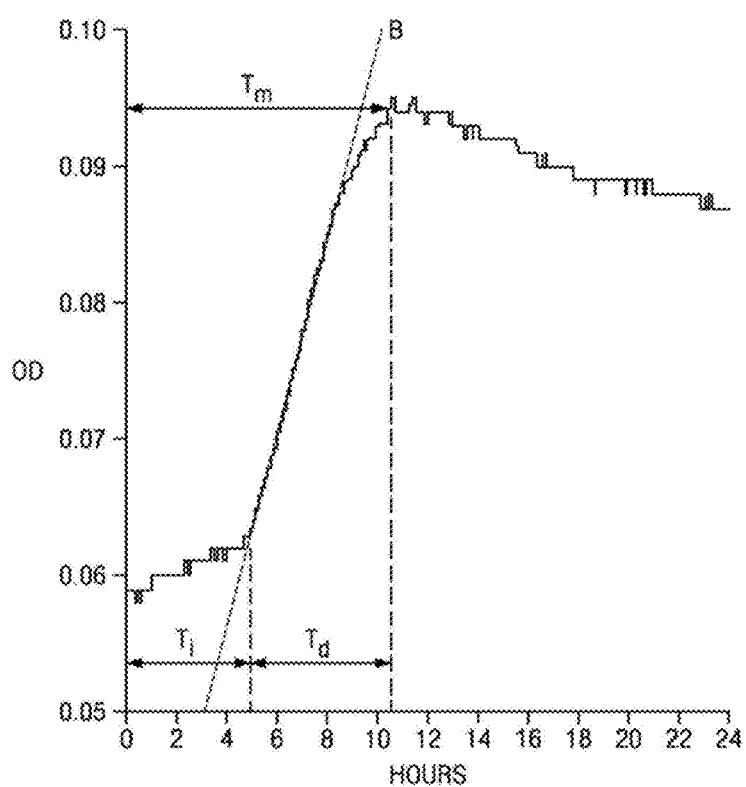
FIG. 2 is a prior art graph showing an example plot of time versus optical density (OD) during a MiCK assay in which an anti-cancer drug induces apoptosis in the cancer cells tested.

Spectrophotometric data may be converted to kinetic units. Kinetic units are determined by the slope of the curve created when the change in the OD at 600 nm caused by cell blebbing is plotted as a function of time. FIG. 1 shows a prior art photomicrograph of a cell. Part A of FIG. 1 shows the cell prior to apoptosis. Part B of FIG. 1 shows the cell during apoptosis when blebbing is occurring. Part C of FIG. 1 shows a cell when apoptosis is complete or nearly complete. FIG. 2 is a prior art graph showing an example plot of time versus optical density (OD) during a MiCK assay in which an anti-cancer drug induces apoptosis in the cancer cells tested.

Figure 3:
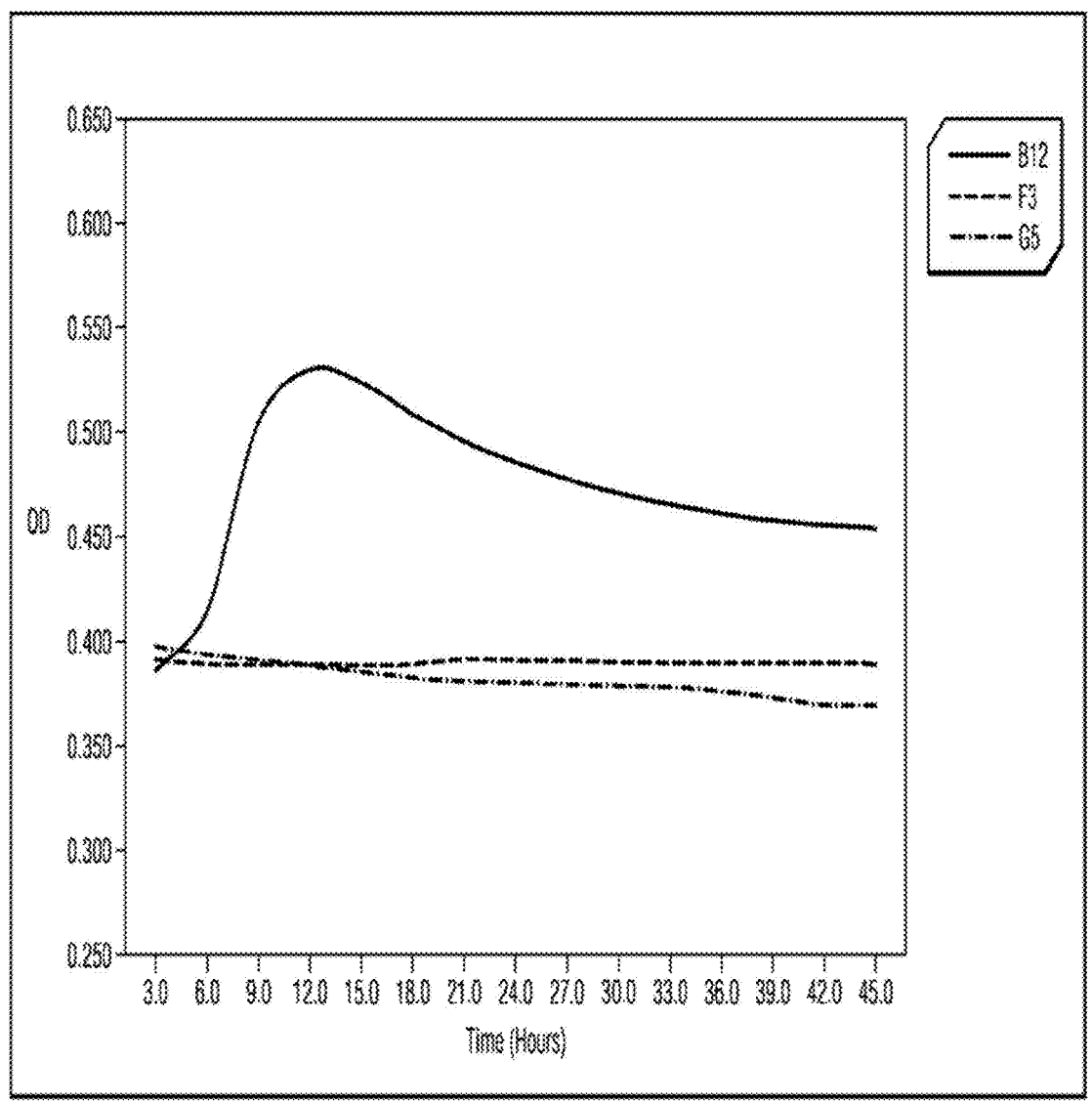
FIG. 3 is a graph showing representative curves for induction of apoptosis, drug resistance, and control cells without drug in a MiCK assay. The curve labeled "B12" shows data representative of cells in which the drug induces apoptosis. The curve labeled "F3" shows data representative of cells that are resistant to the drug. The curve labeled "G5" shows data representative of control cells that did not receive any drug.
Figure 4:
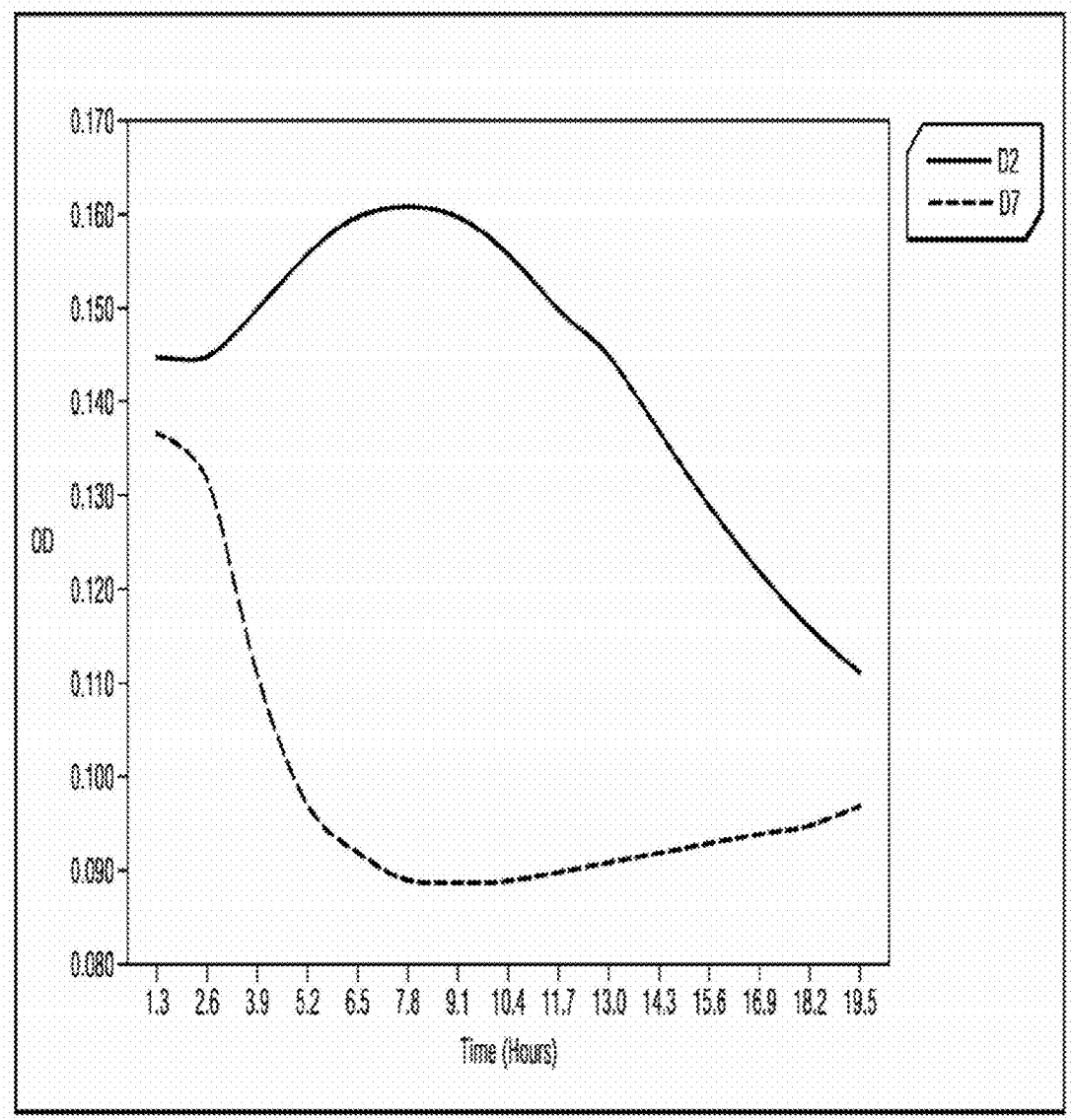
FIG. 4 is a graph showing representative data for induction of apoptosis or necrosis in a MiCK assay. The curve labeled "D2" shows data representative of cells in which the drug induces apoptosis. The curve labeled "D7" shows data representative of cells in which the drug induces necrosis or which otherwise undergo necrosis during the course of the assay.
Figure 5:
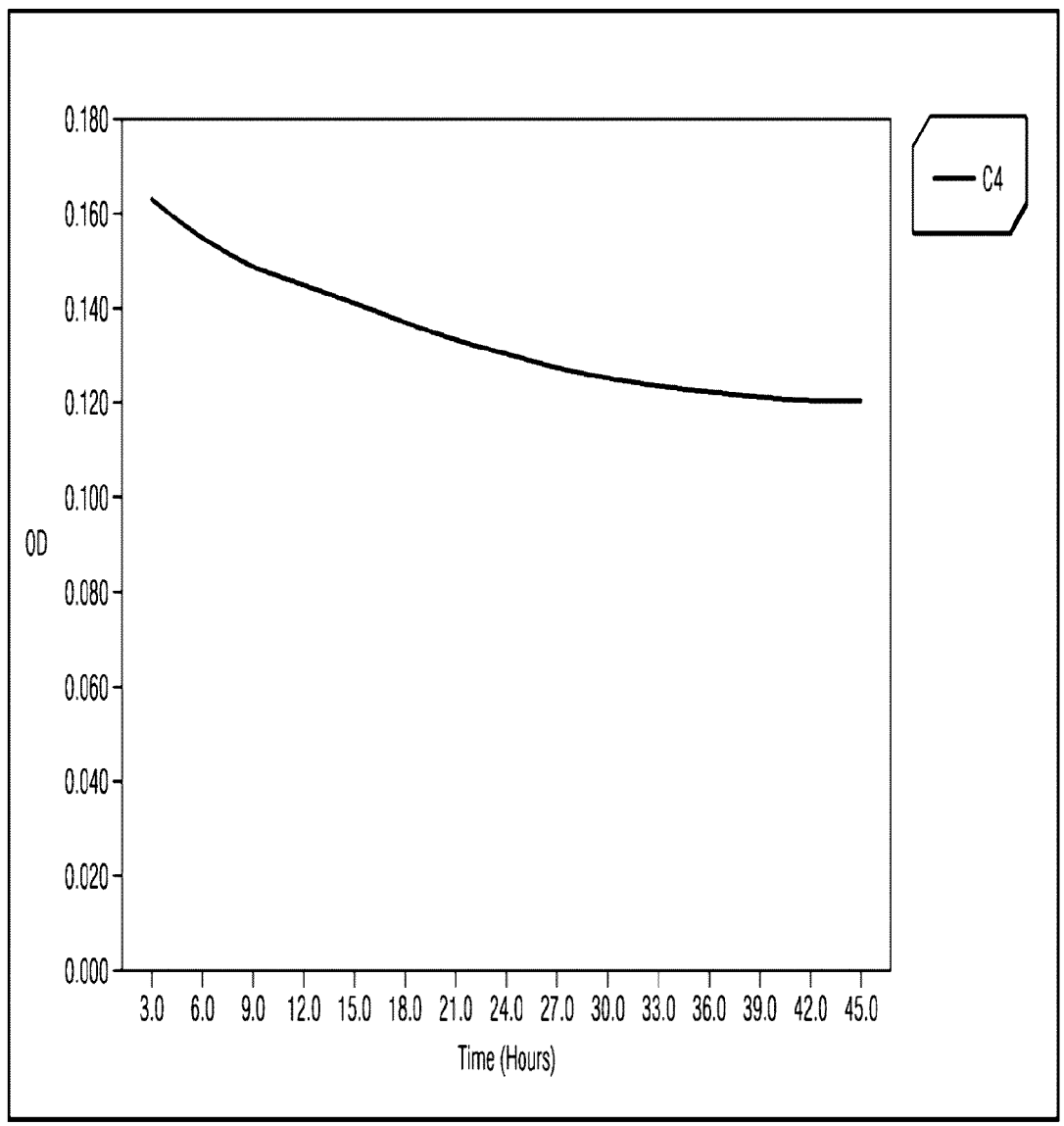
FIG. 5 is a graph showing representative data for general non-drug-induced cell death in a MiCK assay. The curve labeled "C4" shows data representative of spontaneous cell death during the course of the assay.
Figure 6:
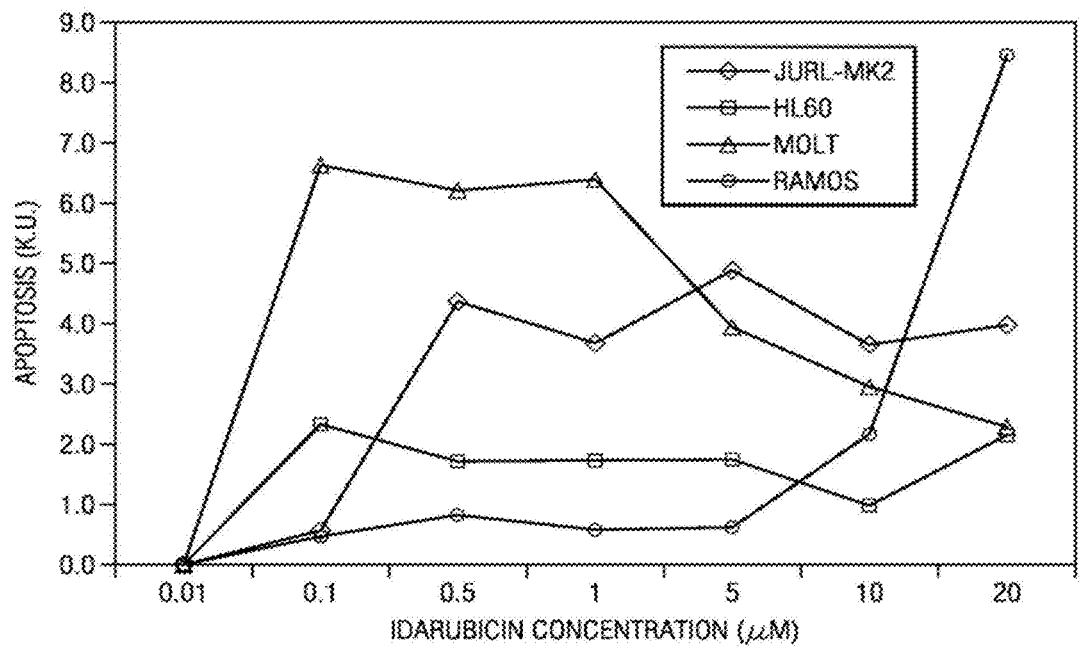
FIG. 6 is a graph showing representative date for the evaluation of the response of known cell lines corresponding to different cancer types to Idarubicin.
Figure 7:
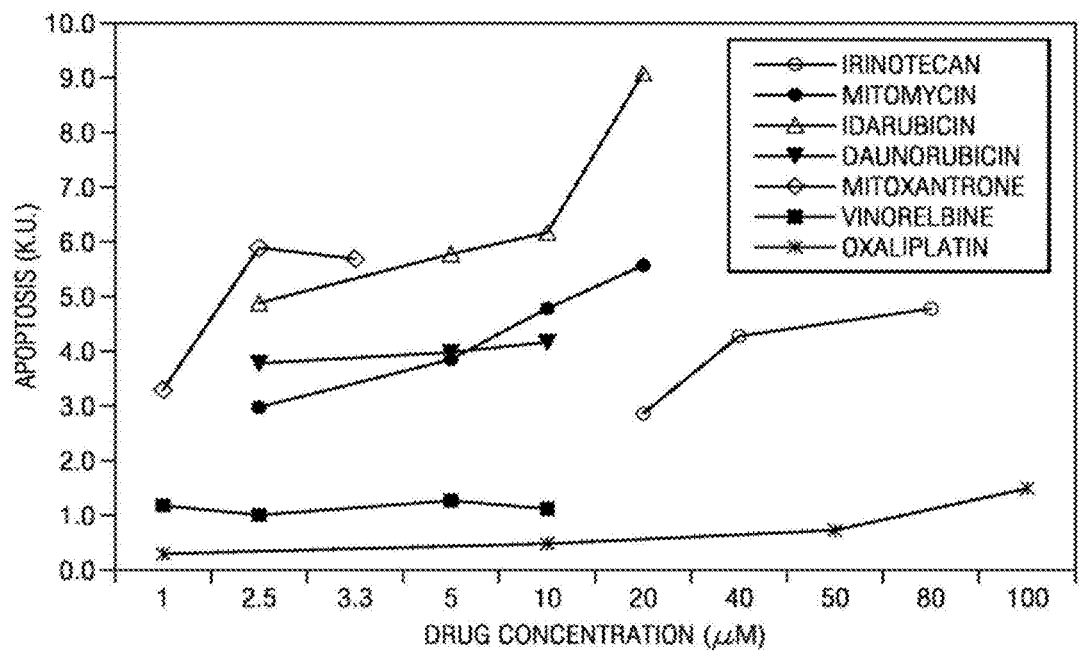
FIG. 7 is a graph showing representative data for the evaluation of the response of the known CAOV-3 ovarian cancer cell line to different chemotherapeutic agents.

Specific information regarding the calculation of kinetic units is provided in Kravtsov, Vladimir D. et al., Use of the Microculture Kinetic Assay of Apoptosis to Determine Chemosensitivities of Leukemias, Blood 92:968-980 (1998), incorporated by reference herein. Optical density for a given drug candidate at a given concentration may be plotted against time. This plot gives a distinctive increasing curve if the cells are undergoing apoptosis. An example of the curve obtained when cells undergo apoptosis is shown in FIGS. 3 and 4. In comparison, if the drug candidate has no effect on the cells (e.g. they are resistant), then the curve is similar to that obtained for a control sample with no drug or drug candidate (FIG. 3) Cell death due to reasons other than apoptosis can also be determined by the current assay and is useful in eliminating false positives from drug candidate screening. For example, cell necrosis produces a distinctive downward sloping curve easily distinguishable from the apoptosis-related curve as seen in FIG. 4. Further, general cell death also causes a downward curve as seen in FIG. 5.

The effectiveness of a drug candidate may be determined by the value of the kinetic units it produces in a modified MiCK assay using a known cell line, or live cells from a specific patient. Kinetic units may be determined as follows:

$$KU = (V\max_{Drug\ Treated} - V\max_{control}) \times 60 \times y / (OD_{cell} - OD_{blank}).$$

Vmax is the maximum kinetic rate, which is the slope of the steep increase in the OD v. time plot when cells are undergoing apoptosis. Vmax in this equation is given in mili-optical density units/hour (mOD/h). $OD_{cell}$ is the initial OD of the control containing cells and $OD_{blank}$ is the initial OD of a blank well containing only medium or medium and drug (the drug may be omitted for some drugs, but for colored drugs in particular it may be included in the blank). y is a coefficient dependent on the cell type being assayed and may be determined experimentally through observation of the cell lines. Further information regarding this equation may be found in Kravtsov, et al.

For the purposes of the present invention as described in more detail herein, and specifically with regard to the ability of an automated system to determine the relative effectiveness of drug candidates, it should be noted that kinetic units (KU) are not necessarily the only basis of making such determinations. Any calculated value which relates to measured optical density in the test wells may also form the basis for assessing whether a drug candidate is effective, provided such calculated value has some correlation to drug candidate activity which induces blebbing and eventual apoptosis. Therefore, in its broadest embodiment, the present invention refers to such a value as an "activity value", and wherein the kinetic units (KU) value, defined by the foregoing formula, is only one example of such an activity value.

In addition to allowing determinations of whether or not a drug candidate causes apoptosis, kinetic unit values generated using the current assay may be compared to determine if a particular drug candidate performs better than or similar to current drugs. Comparison of different concentrations of a drug candidate may also be performed and may give general indications of appropriate dosage. Occasionally some drugs may perform less well at higher concentrations than lower concentrations in some cancers. Comparison of kinetic unit values for different concentrations of drug candidates may identify drug candidates with a similar profile.

Overall, evaluation of an anti-cancer drug candidate may include any determination of the effects of that drug candidate on apoptosis of a cancer cell. Effects may include, but are not limited to induction of apoptosis, degree of induction of apoptosis as compared to known cancer drugs, degree of induction of apoptosis at different drug candidate concentrations, and failure to induce apoptosis. The anti-cancer drug evaluation assay may also be able to detect non-drug-related or non-apoptotic events in the cancer cells, such as cancer cell growth during the assay or cell necrosis.

Any statistically significant positive kinetic unit value may indicate some tendency of a drug candidate to induce apoptosis of a cancer cell. For many clinical purposes, however, drug candidates or concentrations of drugs only able to induce very low levels of apoptosis are not of interest. Thus, a drug candidate with a low KU value, i.e. 1.0 or lower, would indicate that the drug is ineffective, and should not be used in treating a patient, especially in view of the possible side effects and delays in other more effective treatment regimens. Accordingly, in certain embodiments of the disclosure, threshold kinetic unit values may be set to distinguish drug candidates able to induce clinically relevant levels of apoptosis in cancer cells. For example, the threshold amount may be 1.5, 2, or 3 kinetic units. The actual threshold selected for a particular drug candidate or concentration of drug candidate may depend on a number of factors. For example, a lower threshold, such as 1.5 or 2, may be acceptable for a drug candidate able to induce apoptosis in cancer types that do not respond to other drugs or respond only to drugs with significant negative side effects. A lower threshold may also be acceptable for drug candidates that exhibit decreased efficacy at higher concentrations or which themselves are likely to have significant negative side effects. A higher threshold, such as 3, may be acceptable for drug candidates able to induce apoptosis in cancer types for which there are already suitable treatments.

Drug Candidates

The anti-cancer drug candidates may be any chemicals to be evaluated for the ability to induce apoptosis in cancer cells. These candidates may include various chemical or biological entities such as chemotherapeutics, other small molecules, protein or peptide-based drug candidates, including antibodies or antibody fragments linked to a chemotherapeutic molecule, nucleic acid-based therapies, other biologics, nanoparticle-based candidates, and the like. Drug candidates may be in the same chemical families as existing drugs, or they may be new chemical or biological entities.

Drug candidates are not confined to single chemical, biological or other entities. They may include combinations of different chemical or biological entities, for example proposed combination therapies. Further, although many examples herein relate to an assay in which a single drug candidate is applied, assays may also be conducted for multiple drug candidates in combination.

More than one drug candidate, concentration of drug candidate, or combination of drugs or drug candidates may be evaluated in a single assay using a single plate. Different test samples may be placed in different wells. The concentration of the drug candidate tested may be, in particular embodiments, between 0.01 μM and 100,000 μM. The concentration tested may vary by drug type.

Plate and Spectrophotometer Systems

The plate and spectrophotometer may be selected such that the spectrophotometer may read the plate. For example, when using older spectrophotometers, one may use plates with larger wells because the equipment is unable to read smaller-well plates. Newer spectrophotometers may be able to read plate with smaller wells. However, plates with extremely small wells may be avoided due to difficulties in filling the wells and in measuring small volumes accurately. In one embodiment, the diameter of the bottom of each well is no smaller than the diameter of the light beam of the spectrophotometer. The spectrophotometer may make measurement at wavelengths other than 600 nm. For example, the wavelength may be +/−5 nm or +/−10 nm. However, other wavelengths may be selected so as to be able to distinguish apoptosis.

Spectrophotometers may include one or more computers or programs to operate the equipment or to record the results. The spectrophotometer may be functionally connected to a single server or computer, and available to multiple computer workstations through that server, able to control the measurement process, record its results, and display or transmit graphs plotting the optical densities as a function of time for each well. Such functions will be described below with specific reference to the present invention.

Plates designed for tissue culture may be used, or other plates may be sterilized and treated to make them compatible with tissue culture. Plates that allow cells to congregate in areas not accessible to the spectrophotometer, such as in corners, may work less well than plates that avoid such congregation. Alternatively, more cancer cells may be added to these plates to ensure the presence of a monolayer accessible to the spectrophotometer during the assay. Plates with narrow bottoms, such as the Corning Costar half area 96 well plate may also assist in encouraging formation of a monolayer at the bottom of the well without requiring inconveniently low sample volumes. Other plates, such as other 96-well plates or smaller well plates, such as 384-well plates, may also be used.

Cancer Cells

The cancer cells used in the assay may be any established cancer cell line, or live cancer cells from a specific patient. Use of an established cell line helps avoid complications, such as mutations of a portion of the cells, that may be difficult to detect and may cause inaccurate test results. In a particular embodiment, the cancer cells may be from any lines commonly used for cancer drug screening in order to obtain FDA or equivalent government approval of a drug to treat a particular cancer.

In general, for accurate results the cancer cell line may be a known cancer cells line, such as a cell line available from the American Type Culture Collection or similar repository. The known cancer cell line may be verifiable as malignant or as having markers used in the art to identify the cell line. For example, the HeLa cell line is a known cervical cancer cell line. Although not required, in some instances a known cancer cell line will be immortalized.

Multiple cancer cell lines may be tested on the same plate in the current assay. However, cell lines with vastly different growth rates or vastly different susceptibilities to control drugs may be tested on different plates due to differences in adjustment and testing times.

During the assay, cancer cells may not always remain as single cell suspensions. For example, solid tumor lines may attach to the surface of the well and form a layer of cells bonded to one another. This attachment and bonding generally may not interfere with the assay, particularly if cells do not overlap or form clumps in a manner that prevents the spectrophotometer measurements from substantially representing the percentage of total cells that undergo blebbing and eventual apoptosis.

Automation of Drug Effectiveness Determinations

Automation of the processes described above and management of various aspects required in making drug effectiveness determinations can be accomplished as set forth below. In a preferred embodiment, the present invention is a comprehensive software application referred to as the Oncology Personalized Information Engine (OPIE), and it operates in communication with a database server, networked computers, spectrophotometers (sometimes referred to as "readers"), and other peripherals. OPIE includes a graphical user interface (GUI) which allows users to interact with and control the readers, and to see data stored in the database. OPIE also performs all calculations which are necessary to determine the effectiveness of drug candidates on the cancer cells.

Figure 8:
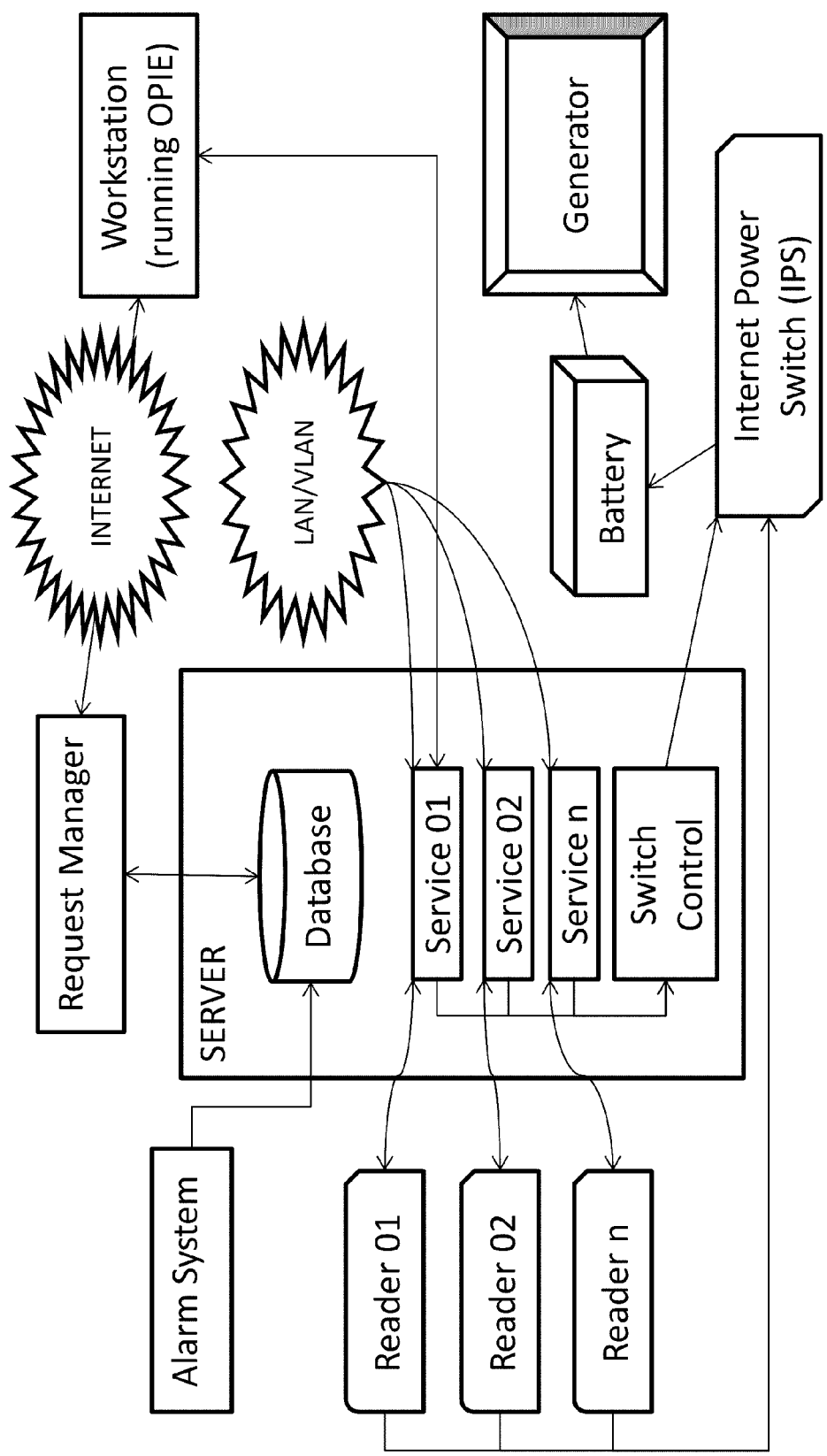
FIG. 8 is a schematic diagram of a preferred embodiment of an overall system depicting computers, database, spectrophotometers (readers), and other components in common communication.

FIG. 8 shows one or more workstation computers which are connected to a server containing a primary database, such as an SQL Server marketed by Microsoft Corporation, over a local area network or virtual local area network (LAN/VLAN). While the database may be located on the server itself, the database may also be located in a remote location and in communication with server. The computers may access the server via the Internet rather than the LAN/VLAN, although any such requests are required to pass through a request manager which authenticates the user's access credentials and isolates the database from the Internet. A preferred embodiment of a relational database structure for the database in FIG. 8 is described in more detail herein with reference to FIGS. 47.

Figure 9:
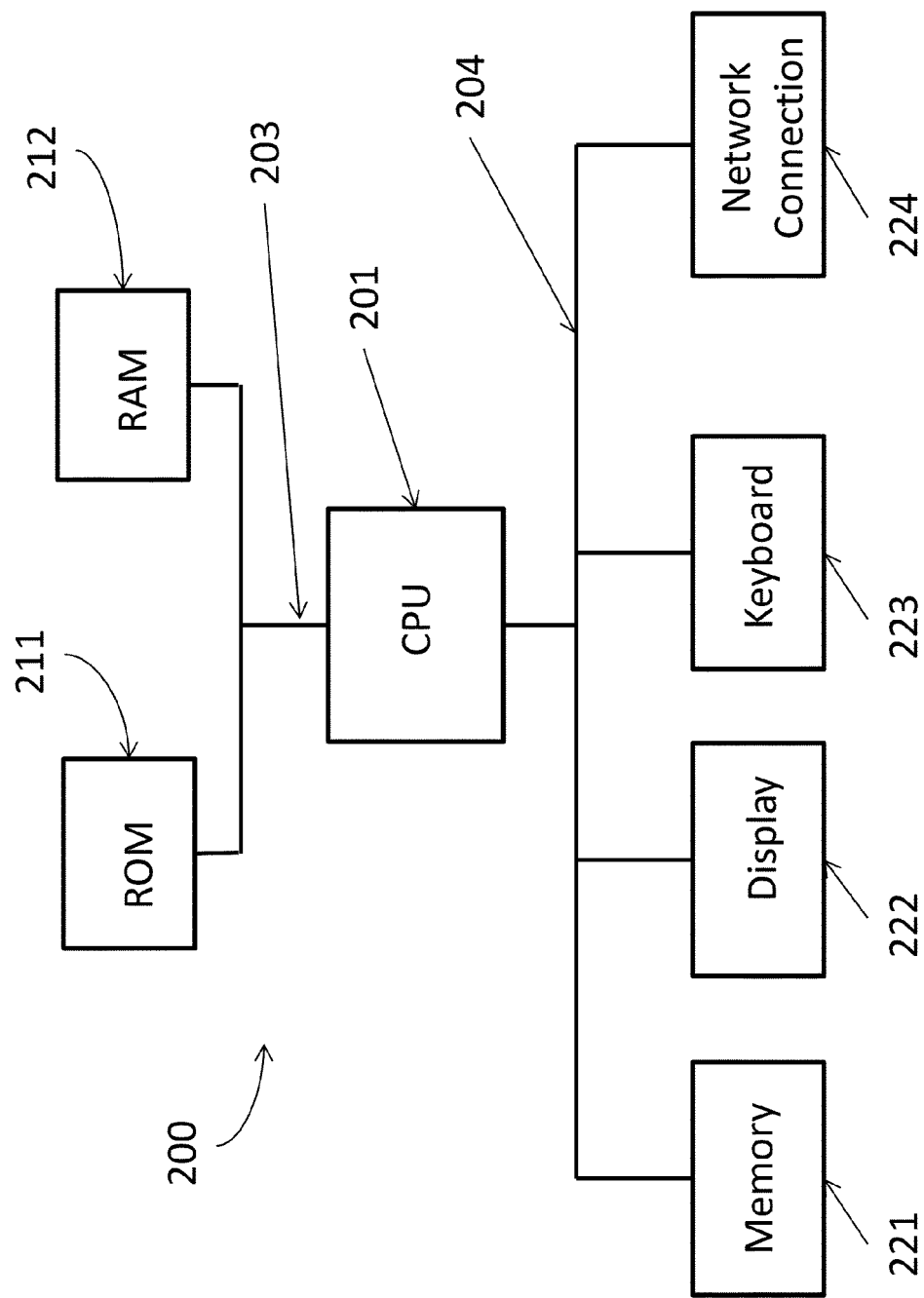
FIG. 9 is a schematic diagram of a computer required for operation of the present invention.

FIG. 9 illustrates an exemplary embodiment of a computer or processing system 200 for use with OPIE. Processing system 200 has a central processing unit (CPU) 201. CPU 201 is a processor, microprocessor, or any combination of processors and microprocessor that execute instructions stored in memory to perform an application. CPU 201 is connected to a memory bus 203 and input/output (I/O) bus 204. A non-volatile memory, such as read only memory (ROM) 211, is connected to CPU 201 via memory bus 203. ROM 211 stores instructions for initialization and other system commands of processing system 200. One skilled in the art will recognize that any memory that cannot be written to by CPU 201 may be used for the functions of ROM 211.

A volatile memory such as Random Access Memory (RAM) 212 is also connected to CPU 201 via memory bus 203. RAM 212 stores instructions for all processes being executed and data operated upon by the executed processes. One skilled in the art will recognize that other types of memories such DRAM and SRAM may also be used as a volatile memory and that memory caches and other memory devices (not shown) may be connected to memory bus 203.

Peripheral devices include, but are not limited to, memory 221, display 222, I/O device 223, and network connection device 224 that are connected to CPU 201 via I/O bus 204. I/O bus 204 carries data between the device and CPU 201. Memory 221 is a device for storing data onto a media. Some examples of memory 221 include read/write compact discs (CDs), and magnetic disk drives. Display 222 is a monitor or display and associated drivers that convert data to a display. I/O device 223 is a keyboard, a pointing device or other device that may be used by a user to input data. Network device 224 is an Ethernet device that connects processing system 200 to a network, and such connections may be wired or wireless. One skilled in the art will recognize that exact configuration and devices connected to each processing system in network may vary depending upon the operations that the processing system performs in the network.

Referring again to FIG. 8, an Internet or remote power switch (IPS) is connected to the server to allow remote rebooting of connected devices. Preferably, the IPS is also connected to a battery which is charged by a generator in the event of emergencies or other power outages. A plurality of spectrophotometers, or readers, are electronically in communication with the IPS, and they are responsible for measuring the OD of the well contents as described earlier herein. A switch control resides between the server and the IPS so that communications between the reader services and the IPS can occur. For example, each reader includes a unique identifier (ID), and if a reboot of a particular reader is required, the port number of that reader in the database is accessed and the reboot is accomplished.

A number of services are installed on the server, such that each service corresponds to a particular reader. Those services allow communication between the server, the readers, and the OPIE software on the computers, and they translate commands from OPIE into commands that the readers will understand and act upon. When a reader sends data to the server, such as an OD reading, the associated service parses that data and acts according to the last command sent to the reader. The service also sends the result (such as confirmation or failure) of a command requested by OPIE back to OPIE once the reader has executed the command. Likewise, every command sent to the readers via OPIE are issued by the service correlating to its particular reader. Importantly, because each service controls only its particular reader, if one service crashes or otherwise becomes inoperable, the remaining services and readers will remain operable and subject to monitoring. Also, while an assay is running, each service is self-monitored, meaning that if an expected event does not occur, then a request to reboot the reader will be sent to the switch control, and the assay will then restart at the last successful read. A separate alarm system is also provided, comprising an electronic alarm in communication with the database, wherein the alarm sends a notification to a designated recipient upon detection of an anomaly in optical density data being stored to the database. For example, if an assay is running, the alarm system will check the database at some predetermined time interval, perhaps 20 minutes. If an expected reading is not recorded in the database, the alarm system notifies the lab manager or other appropriate personnel by telephone or electronic communication to advise of a problem. During an assay, every reading performed by a particular reader is parsed and stored in the database by its respective service.

Figure 10A:
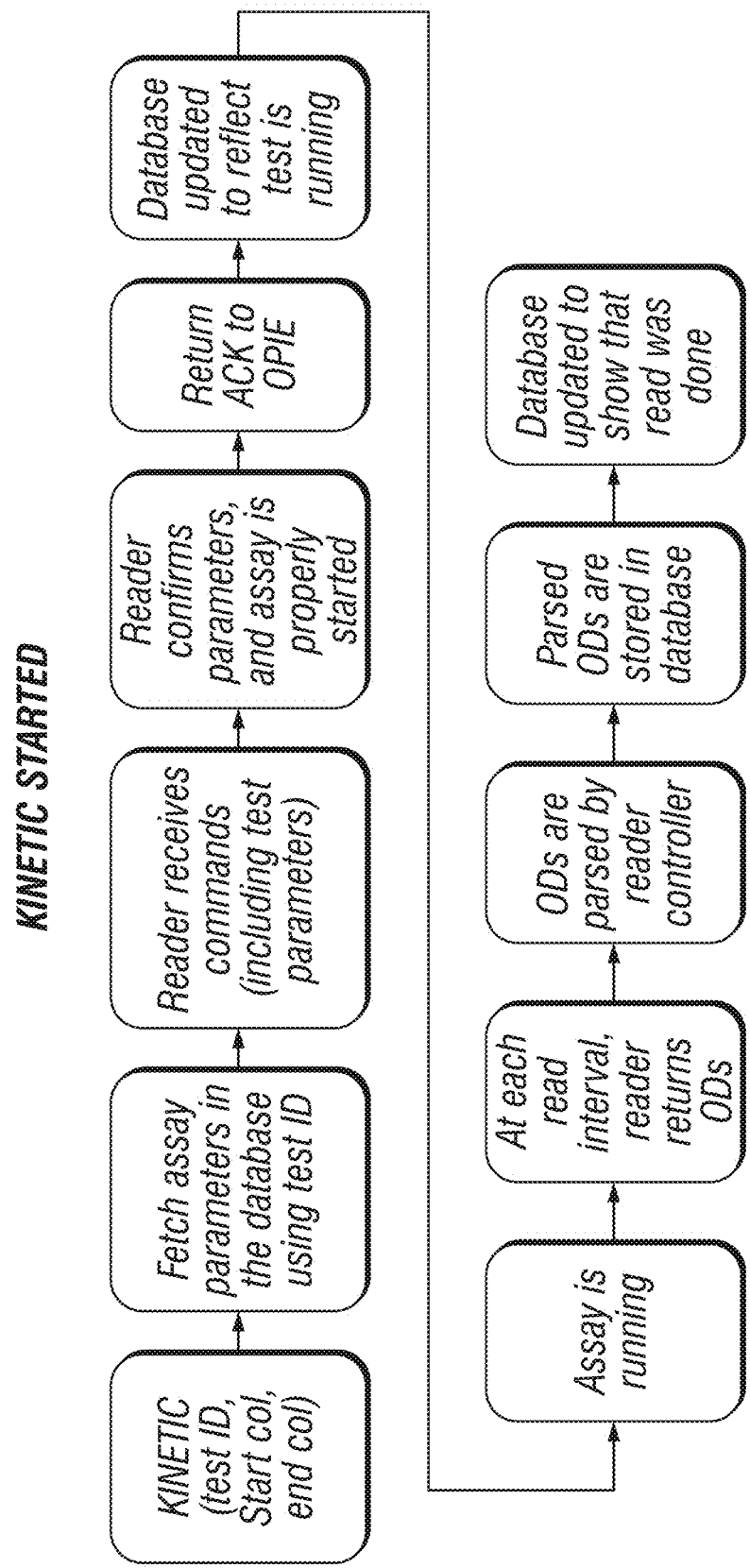
FIGS. 10A-10C are flowcharts depicting typical operational modes of the system in accordance with a preferred embodiment of the present invention.
Figure 10B:
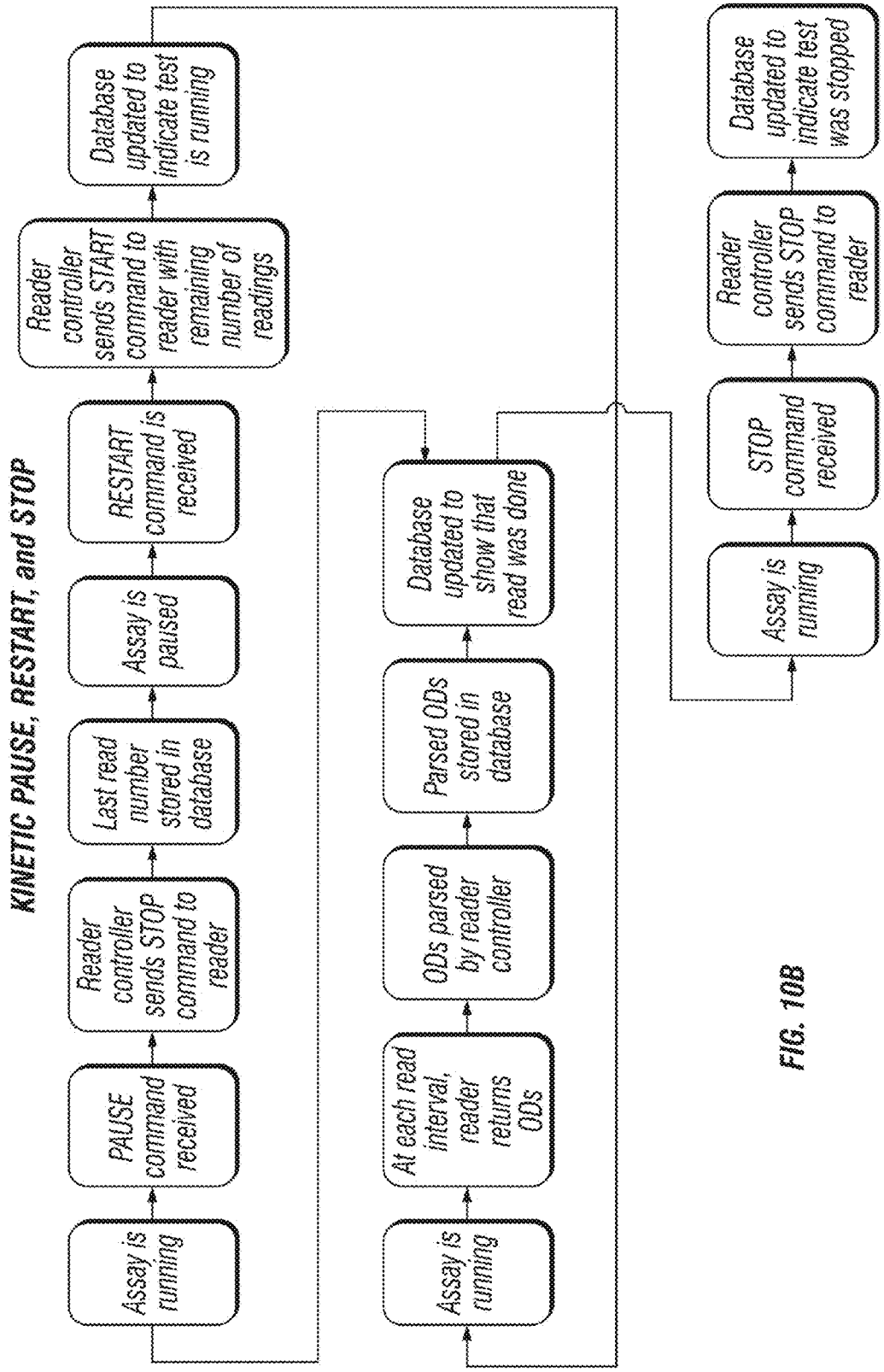
Figure 10C:
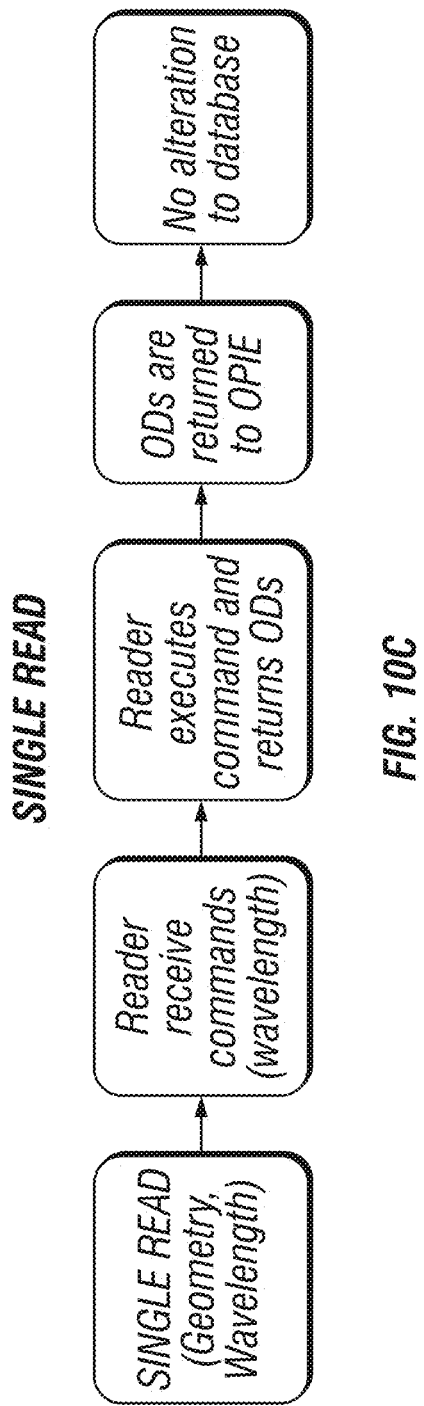

FIGS. 10A-10C are flowcharts depicting typical operational modes of the system in accordance with a preferred embodiment of the present invention. With reference to the services residing on the server, the following explanation will describe an example of a server thread in operation. First, the service listens for an incoming connection from OPIE, which may include a number of different commands. For example, a "Single Read" is a call to the "single read" method of the reader controller, and instructs the reader to perform a measurement of OD for the entire well plate, with accompanying inputs of wavelength and geometry, but only one OD is measured, and all ODs are returned to OPIE. Another command may be to "Start Test", which calls the "kinetic" method of the reader controller and instructs the reader to start an assay. Another command may be "Switch", which calls the "switch off" method of the reader controller, and turns off the reader. A "Pause" command calls the "pause" method of the reader controller, and instructs the reader to temporarily stop the assay and remember where it left off. A "Restart" command calls the "restart" method of the reader controller, and instructs the reader to restart an assay which had been paused. Finally, a "Stop" command calls the "stop" method of the reader controller, and instructs the reader to stop in its entirety. In each case of a command being issued by a user through OPIE, an acknowledgement is sent back to OPIE with an "ACK" signal to indicate successful execution, or a "NAK" signal to indicate unsuccessful execution.

The database can be accessed directly by the services, the switch control, and by OPIE on the computers, but only if the computer is operating over the LAN/VLAN. If a computer running OPIE outside of the LAN/VLAN, any communications with the database must be handled via the request manager, as indicated above.

Figure 11:

With respect to the OPIE software and its interface, OPIE is constructed from the Java programming language developed by Oracle Corporation and uses the Java Virtual Machine GVM), although it can be compiled and operating with other suitable platforms. When OPIE is started, an initial screen is displayed in accordance with FIG. 11. To access OPIE, a user name and a password are necessary. If the user name or password is incorrect, a red message will appear, requiring a reentry of the correct user name and password. A laboratory manager and/or the medical director are typically responsible for creating the user accounts, wherein users have differing access depending upon their rights to edit data or control the running of assays. Once the user has been authenticated, a plurality of selectable upper tabs will be unlocked, namely: LOG IN, TESTS, PROJECT, PATIENT, and OTHERS. Some tabs may remain locked depending on the user level. The Check Tracking button conveniently located on the opening page of FIG. 11 will open a browser window that includes all the shipment tracking numbers that are registered in the database that have activity.

Figure 12:
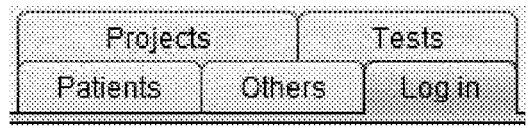

In a preferred embodiment, OPIE is organized into the five main sections indicated above, and represented by tabs as shown in FIG. 12. For example, the LOG IN tab allows the user to open a connection to OPIE and to log out. The TESTS tab allows the user to create, edit, modify, and delete tests. The PROJECT tab allows the user to categorize tests under a specific name. The PATIENT tab allows the user to create, edit, modify and delete patient related data, which typically includes reports and images related to the tests. The OTHERS tab allows the user to modify the program settings and use complementary modules, including single reads, package tracking, management of cell lines, password changes, and the like.

Editing Test Parameters

Figure 13:
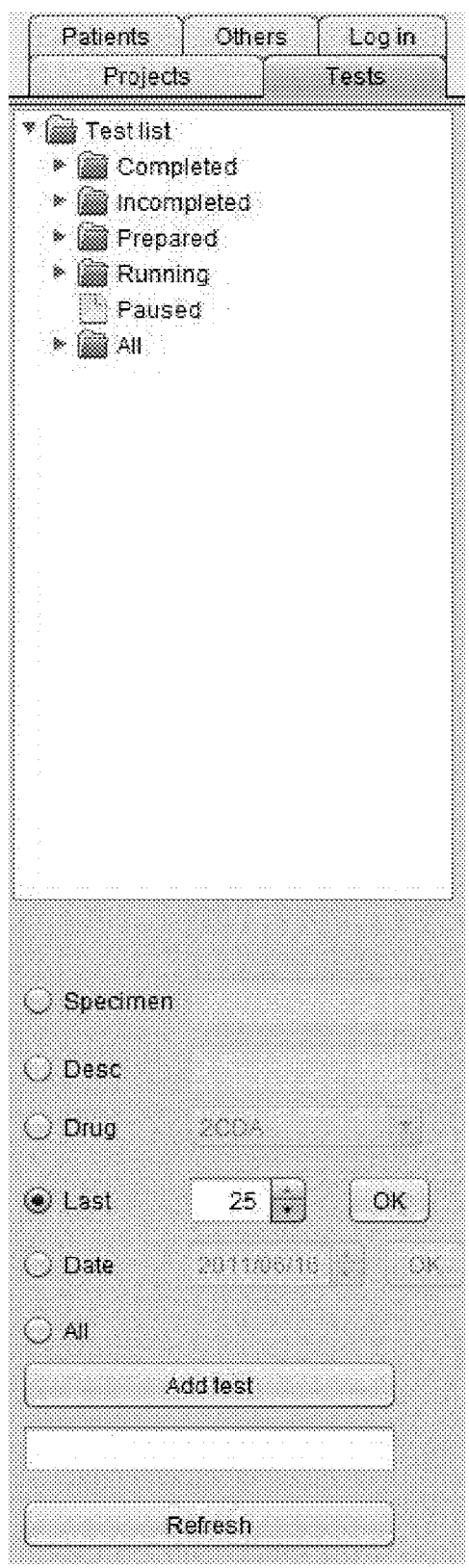

In OPIE software, a test (sometimes referred to herein as a "kinetic") represents a well plate that goes through the MiCK assay from the beginning of a kinetic to its end. Under the TESTS tab, shown in more detail in FIG. 13, the tests are categorized by their states, of which there are five different categories. A category of Complete is a complete test that went through a complete MiCK Assay. A category of Incomplete is a test that was stopped during the kinetic activity. Although a test may be Incomplete, calculations can still be performed if enough data was accumulated. A category of Prepared is the first state of any test, and indicates that the kinetic has not yet started. A category of Running means the test is in the data acquisition phase, e.g. the well plate is inside a spectrophotometer (or reader) and the kinetic is running. A category of Paused means the test was in the data acquisition phase, but a user has set this test on pause, and the kinetic is stopped until the user restarts the kinetic. To refresh the content of the test list, e.g. to see if another user created a new test on another computer, the Refresh button can be selected. Preferably, each of the categories can be graphically represented by an icon which corresponds to the state, such a "stop" button, "pause" button, or similar visual indicia that is familiar and easily recognizable to a user.

The lower section of the TESTS tab enables the user search for a test that corresponds to a specific criteria, such as Specimen (tests associated with a specific specimen), Desc (tests with a specific description), Drug (tests that contain a specific drug), Last (the last created tests), Date (tests created on a specific date), and All (showing all tests, regardless of criteria). A test can be added by the Add Test button by entering a description in the adjacent field, and a new test will appear in the Prepared category as described above.

Figure 14:
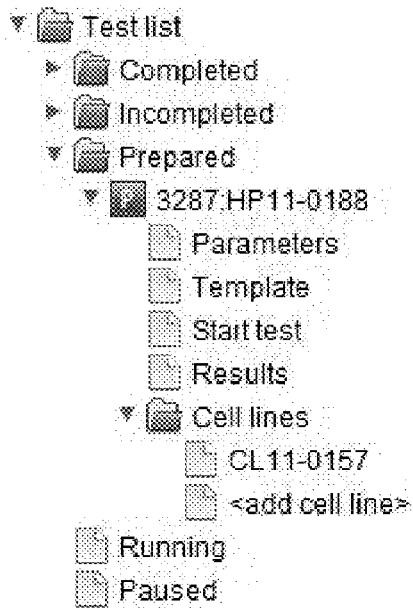
Figure 15:
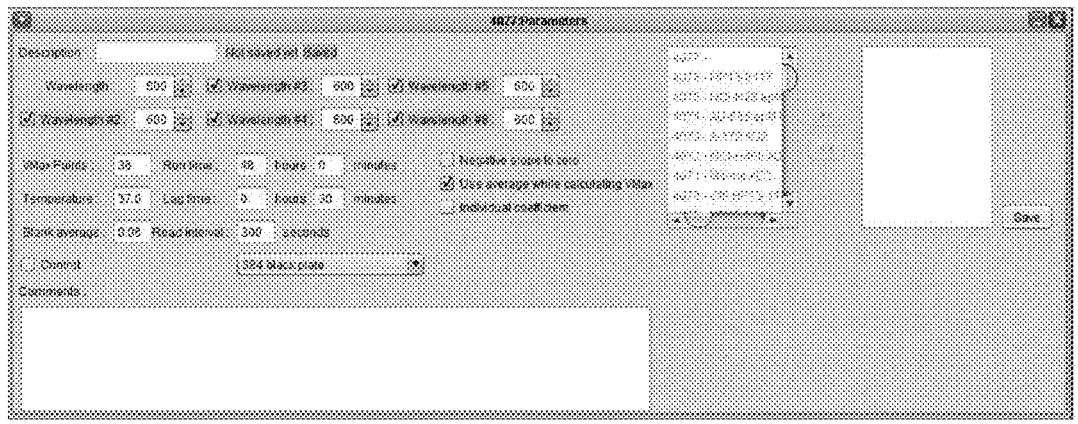

Tests can be edited by selecting the folder icon for Test List, and then further selecting one of the categories based on state, as shown in FIG. 14. If the user has sufficient credentials, the test can be deleted, or it can be edited by selecting the Parameters name, and then using the interface shown in FIG. 15. A test contains many parameters which can be edited, including the following parameters in a preferred embodiment:

Description: The Test's General Descriptions.

VMax Points: This parameter is used during the kinetic units (KUs) calculation, wherein the VMax Points is the distance used to calculate the slopes. For example, a value of 36 means that a slope will be calculated between read number 6 and 42, 7 and 43, etc.

Temperature: The temperature of the spectrophotometer's incubation chamber during the kinetic.

Run time: The duration of the kinetic in hours and minutes.

Lag time: The OD collected during this interval will be ignored during the calculation. For example, a lag time of 30 minutes means that for 30 minutes, the first 6 reads will not be used to calculate the KUs if the interval between reads is set to 5 minutes.

Read interval: The time between each read during the kinetic.

Blank average: This value will be used if the template does not include any blanks.

Negative slope to zero: If this is selected, during the calculation if the control's slope is negative, the value of the slope will be substituted for 0. A negative control slope will boost the KU value for a sample, because it is subtracted from the Vmax.

Use average while calculating VMax: If this option is selected, during the calculation of the slopes the software will use the average of 3 OD for point n and n+VMax to calculate the slopes.

Plate type drop-down box: Indicates the type of well plate being used.

Wavelength: The wavelength used by the spectrophotometer in nanometers (nm). It is possible to assign up to six wavelengths. A reading will be performed for every wavelength selected. Every wavelength must be unique and must be set between 200 and 999 nm, although the more common wavelength for many tests will be 600 nm.

Control: Indicates if this test contains a control cell line. To indicate which tests use this test as a control, one or more tests are selected from the list on the right-side of FIG. 15, and then moved to (or removed from) the far right box using the directional control buttons.

Comments: A more detailed description of the test or other notes.

Once all desired edits to the test parameters have been completed, the Save button is selected, and the new test parameters are recorded to the database.

Figure 16:
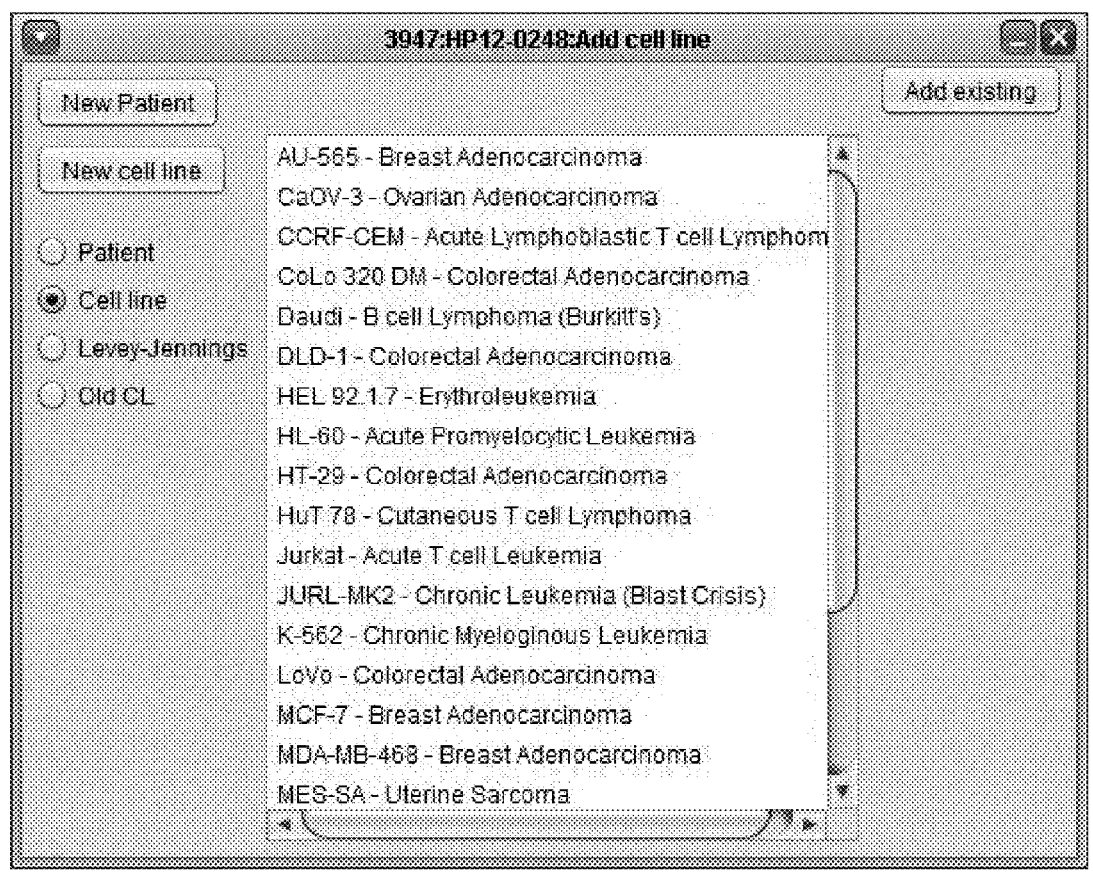

Templates can also be edited, but a cell line must first be assigned to the test. Selecting <add cell line> under the Cell Lines folder in FIG. 15 will open a new box as shown in FIG. 16. To create a new patient or new cell line, the user selects the New Patient or New Cell Line button. To add an existing patient or cell line, the user selects from the list, and then selects the Add Existing button at the top right of the box. The selected cell line or patient will now appear under the Cell Line folder of the test. The cell line represents a pre-defined established cell line, and the name of the cell line will be used to identify the wells in the templates instead of an auto-generated number. To use a custom cell line that uses an auto-generated number, the user would select the Old CL button and choose from the list that appears.

Alternatively, if the test must contain a control cell line in order to generate a Levey-Jennings plot, the user must select a cell line under Levey Jennings list. A popup decision box will appear asking if the test's template should be appended with the template associated to the selected cell line. Selecting Yes will only overwrite the wells in the columns allocated for Levey-Jennings, such as columns 15 to 18, leaving the other wells untouched.

Figure 17:
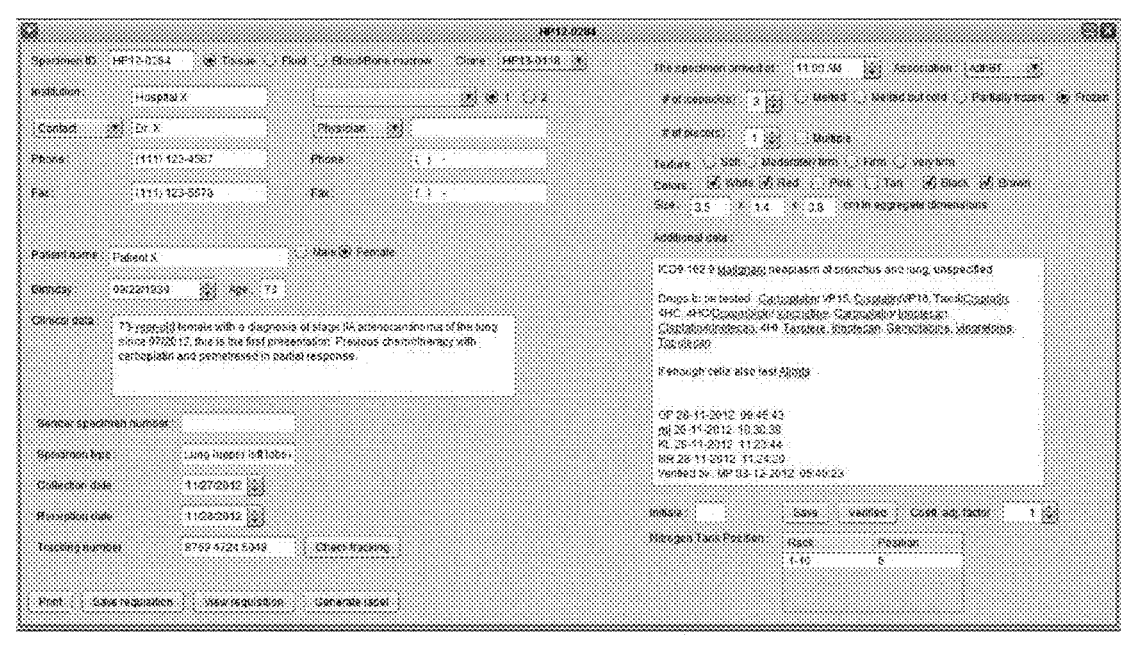

To edit the cell line, the user selects the desired cell line from the Cell Line folder, which opens an interface as shown in FIG. 17. As can readily be seen, the interface includes numerous familiar and self-explanatory fields related to information about the cell line, along with details regarding the specimen, patient information, and instructions about which drugs may be tested. Regarding certain more notable features, the Clone drop-down box allows the user to populate all fields with information from another patient. The Print button is used to create a ready-to-print portable document format (PDF) file containing all patient data. Modifications are recorded by typing the user's initials in the Initials box and selecting the Save button, and the initials are automatically appended at the end of the Additional Data field. As an extra precaution, a Verified button is included to signify that all data is correct.

The coefficient adjustment factor is used to modify the coefficient of the specimen (and in every test that this specimen was associated). A value between 0 and 1 will lower the coefficient and above 1 will raise the coefficient. In most cases, it is important that the medical director or one suitably knowledgeable about the specimen can adjust the coefficient, because it is dependent on the cell type being assayed and is determined experimentally through observation of the cell lines, as noted in Kraystov, et al.

The upper right side of the interface is used to describe the specimen and the specimen's shipping conditions. The fields of this section will vary according to the type of specimen that was selected in the upper left section, e.g. tissue, fluid/effusion, or blood/bone marrow.

If cells from this specimen were frozen and stored in liquid nitrogen, the positions of every tube will appear in the lower right table. If no cells were frozen, the lower right table will remain disabled.

Figure 18:
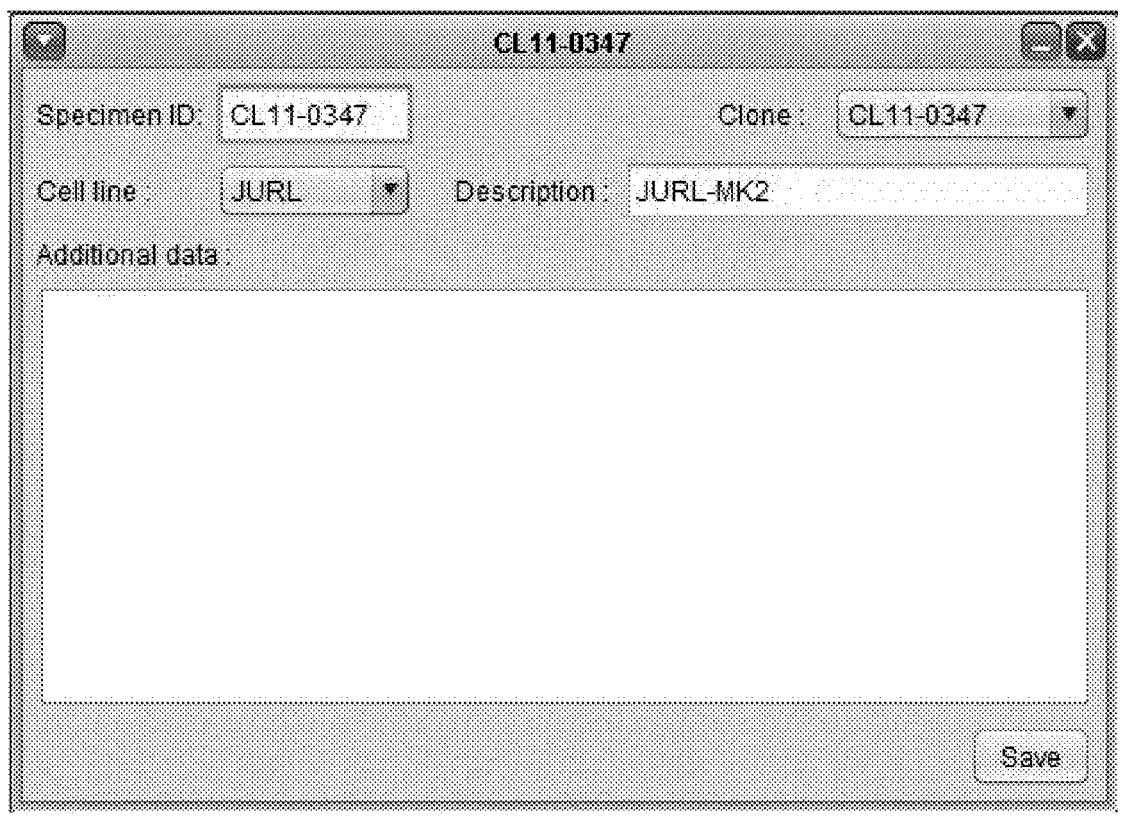

Importantly, if the cell line is not a patient, the interface of FIG. 18 will appear instead. The cell line is selected from the Cell Line drop-down box. Data from another cell line can be copied by selection of the desired cell line in the Clone drop-down box. When completed, the Save button is selected and the interface is closed. Also, a patient or cell line can be assigned to multiple tests. To remove a cell line from a test, the cell line is selected and deleted using the Delete key on the keyboard, but this does not delete the cell line itself from the database.

Editing Templates

Figure 19:
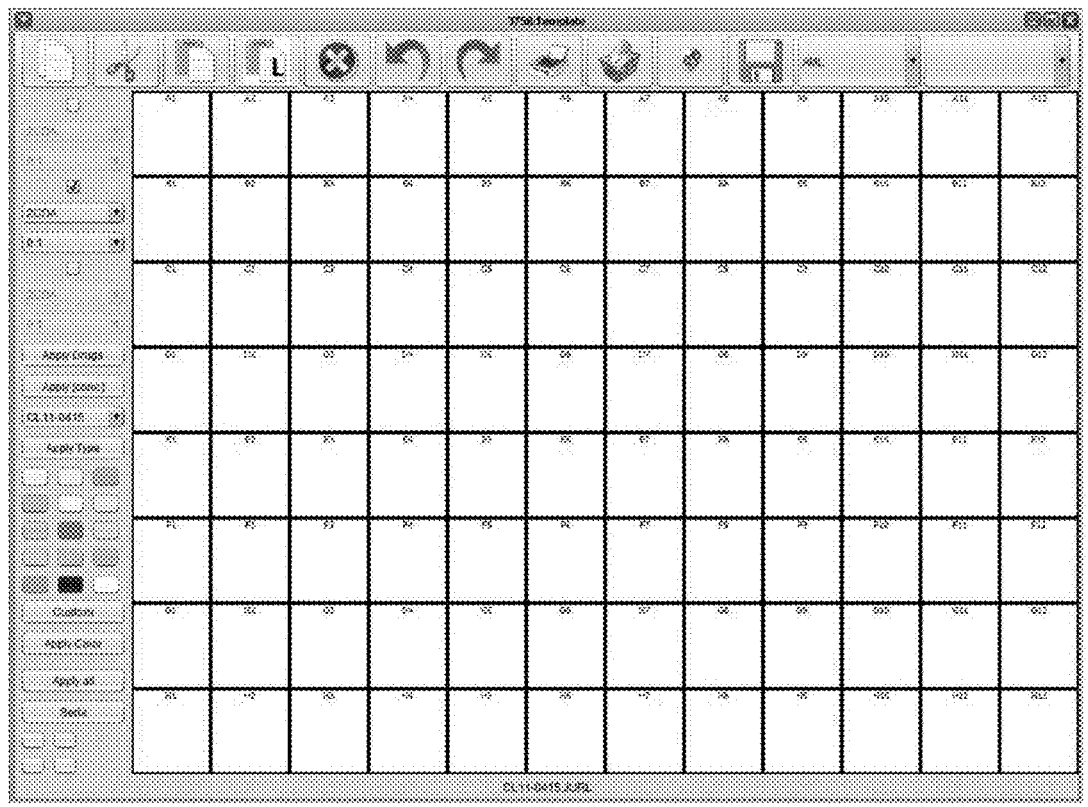

For any specific test, its template can be edited as shown in the interface of FIG. 19, which displays a virtual well plate that models a physical well plate whose contents would be subject to OD measurements in the reader. For example, a physical 96-well plate is an 8×12 grid of wells having well locations each designated by an alphanumeric character. The first row of 12 wells are designated A1-A12, the second row of wells are designated B1-B12, until the last (eighth) row wells are designated H1-H12. This arrangement is duplicated in the virtual well plate interface of FIG. 19.

Figure 20:
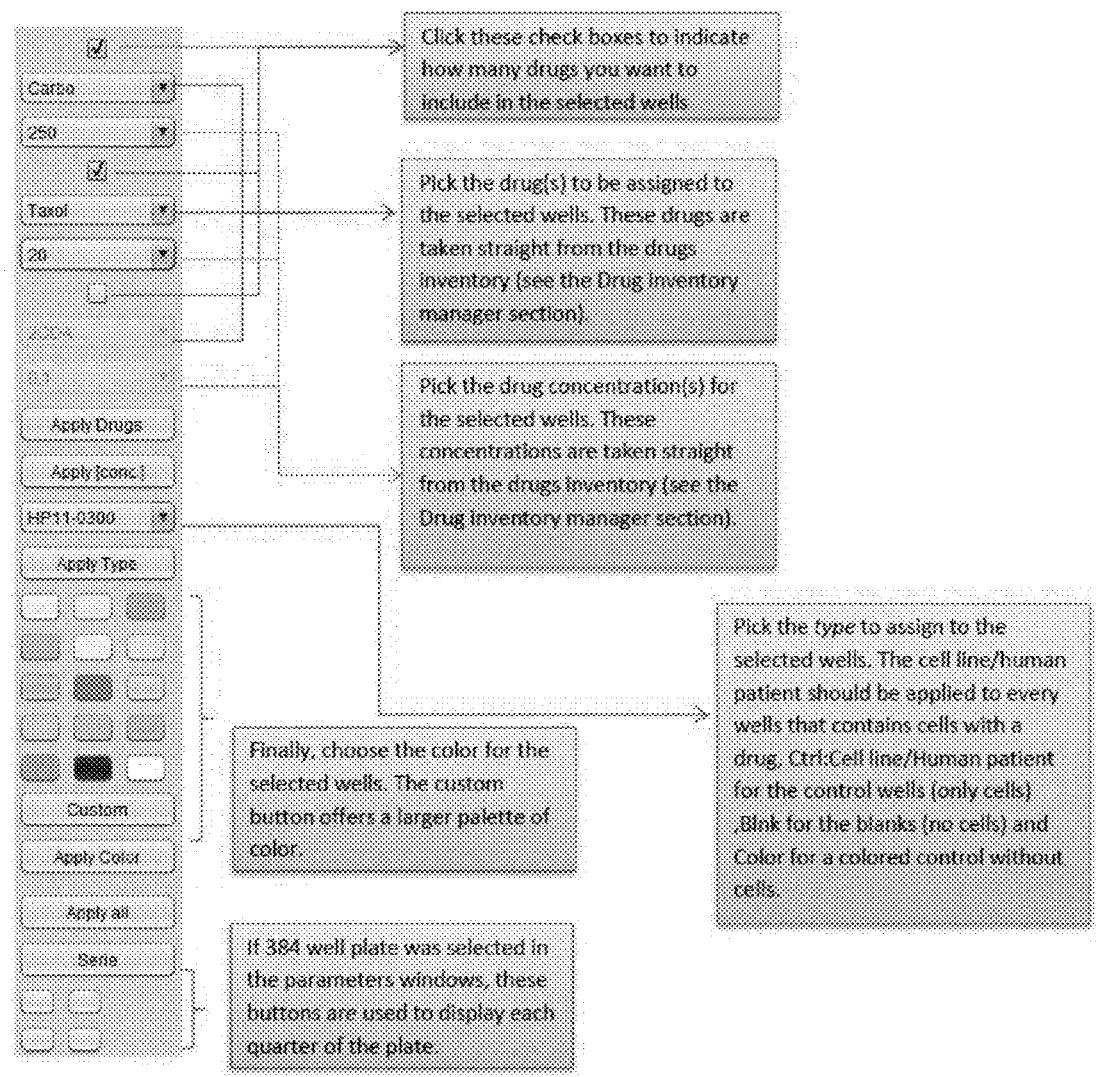

The left-side panel of the interface provides various options for defining the contents and display of the individual wells, and an edit menu bar resides above the wells. Each well contains up to three drugs and concentrations, as well as a type. Any well selected by the user is framed with a red border, and the contents of that well are shown in the left panel. Additional selection options familiar to the user are also available, including multiple well sections and selection ranges, which allows similar parameters (drugs and concentrations) to be applied to multiple wells simultaneously. FIG. 20 provides a more detailed view of the template editing panel indicating the functions available to the user. Note that if a 384-well plate is used, the four buttons at the bottom of the panel allow selection of each quarter portion of the plate. For example, selection of the upper left button displays wells A1-H12, similar to the wells shown in FIG. 19, while selection of the upper right button displays wells A13-H24, selection of the lower left button displays wells I1-P12, and selection of the lower right button displays wells I13-P24.

To apply the selected changes, the user selects the appropriate Apply button. For example, the individual Apply buttons will only apply their respective field in the selected wells, while the Apply All button will apply the drugs, concentrations, colors, and type. A selected drug, concentration or type can also be applied by pressing the Enter key after the selection.

The Series button is used to create a series of dilutions, e.g. tests for various concentrations of the drug, such as Carbo 250, 500 and 750. The desired wells are selected along with the lowest concentration desired (as shown in the top drug, Carbo 250, of FIG. 20), and when the Series button is selected, all the selected wells will be assigned with the selected drug(s) and concentration(s) in ascending order.

The edit menu bar at the top of FIG. 20 includes a number of editing options and icons which should be familiar to a user having experience with conventional programs. For example:

Copy (Ctrl+C): Puts all the selected wells in the memory buffer.

Cut (Ctrl+X): Puts all the selected wells in the memory buffer and clears all the selected wells.

Paste (Ctrl+V): Pastes the wells copied into the memory buffer in the first selected wells. The pattern of the buffered wells will be preserved.

Paste Line (Ctrl+L): Pastes the wells copied into the memory buffer in the first selected wells. All the selected wells will be pasted consecutively.

Clear wells (Del): Clears the contents of every selected well.

Undo (Ctrl+Y): Undo the previous action, which can be performed multiple times depending on how many modifications were done.

Redo (Ctrl+R): Redo an action that was undone, which can be performed multiple times.

Print (Ctrl+P): Copies the template in a ready to print PDF file. The PDF will be saved in the Templates folder of the OPIE directory on the local computer.

Print drug list: This will produce a list of all non-fresh drugs included in this template, including dilution lot number, expiration date and localization. The PDF will be saved in the Drugs folder of the OPIE directory on the local computer.

Save (Ctrl+S): Saves the current state of the template. If the window is closed without saving the last modifications, the user is prompted to save. If No is selected the template will not be saved.

Figure 21:
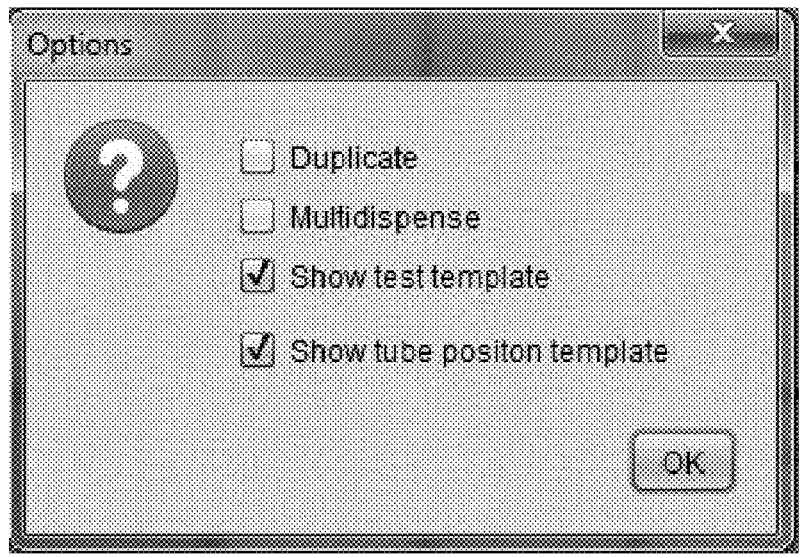

Create .dws file (EP button): Creates a .dws file format of the template to be used with epMotion, which is an automated pipetting system marketed by Eppendorf International. The .dws files will be saved in an appropriate folder in the local computer connected on the epMotion system, and the file will then be available in the patient folder of epBlue. A pop-up box shown in FIG. 21 will appear with the following options.

Duplicate: The pipetting system robot will deliver drugs to two distinct plates.

Multi-dispense: Duplicate drugs will be dispensed in multi-dispense mode. If not selected, pipette mode will be used instead.

Show test template: Displays a printable test template.

Show tube position template: Displays a printable tube position template. This template indicate placement of the drugs' aliquots in the thermal racks.

Figure 22:
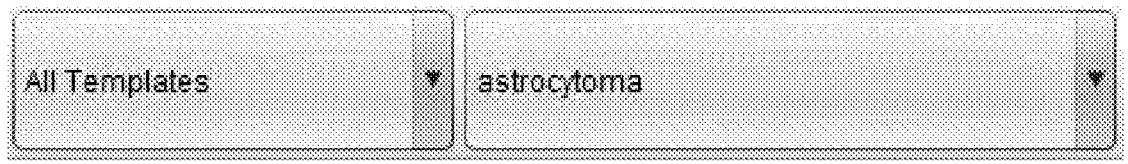

Finally, the right-most portion of the edit menu bar includes two drop-down boxes shown best in FIG. 22. These selections will replace the current template by a template from the default template list. The first box is used to select a template category, and the second box is used to select the specific template. To clone an existing test, the Clone option can be selected from the first drop-down box, and then the user selects the test to be copied. A popup window will ask if the drugs should be arranged in the same order as the associated .dws file.

Starting a Test

Figure 23:
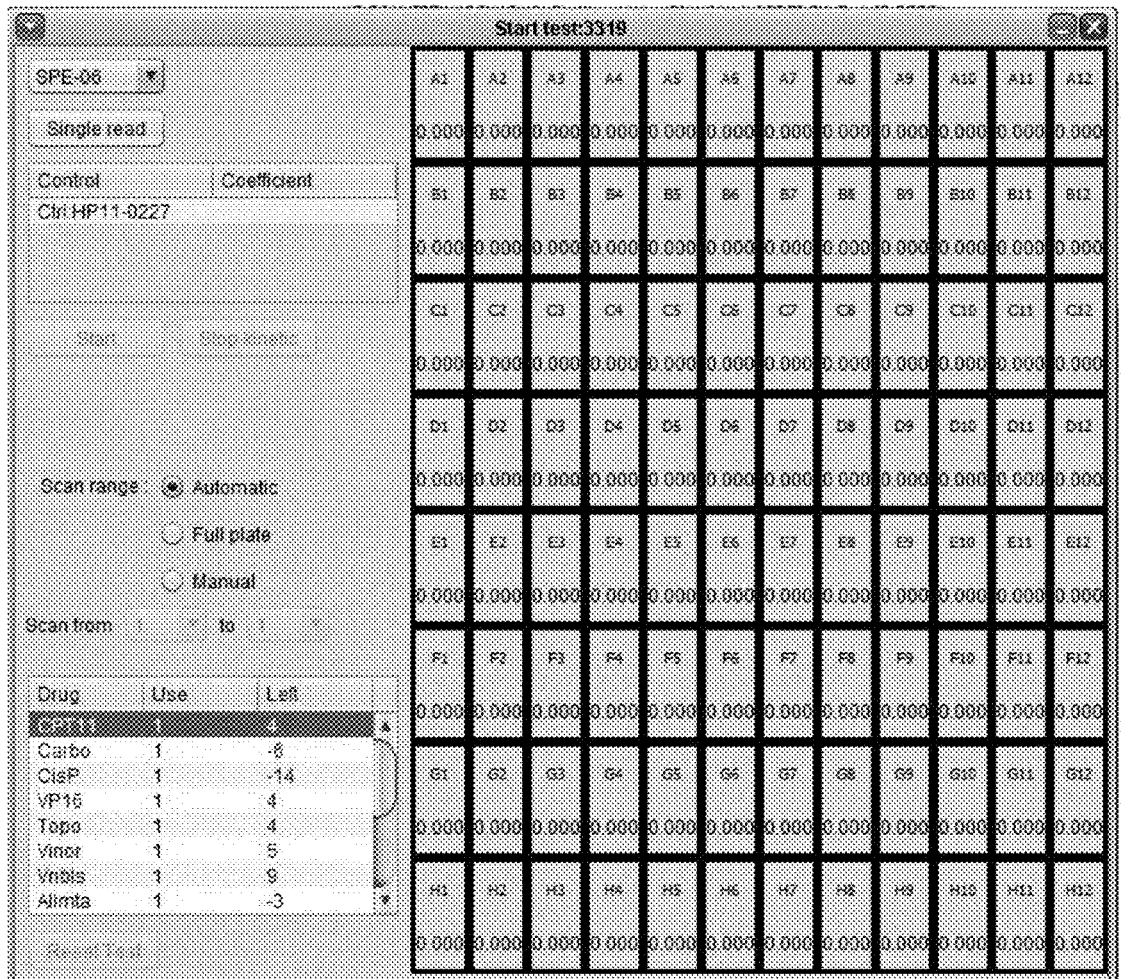

A test (or kinetic) is started by selecting the Start Test option on the left panel, which displays a Start Test interface to the user, similar to that shown in FIG. 23. The first step is to select the reader that will be used for the test, an example of which is "SPE-06" shown in the figure. If a reader is not available, it means that the reader is busy, its controller is not installed on the server, its service is not running, or that a 384-well plate was selected and the reader does not supports this type of plate.

Before starting a test, a Single Read must be performed to determine the coefficient applicable to the test. The user selects the Single Read button in FIG. 23 to calculate the coefficient. If no controls are assigned in the template, a warning message will appear, which prevents the user from proceeding with the test until at least one control is assigned in the template. If the server does not respond, a warning message informing that the connection timed out will appear, meaning that the reader is not turned on or that the reader service is not running properly.

Figure 24:
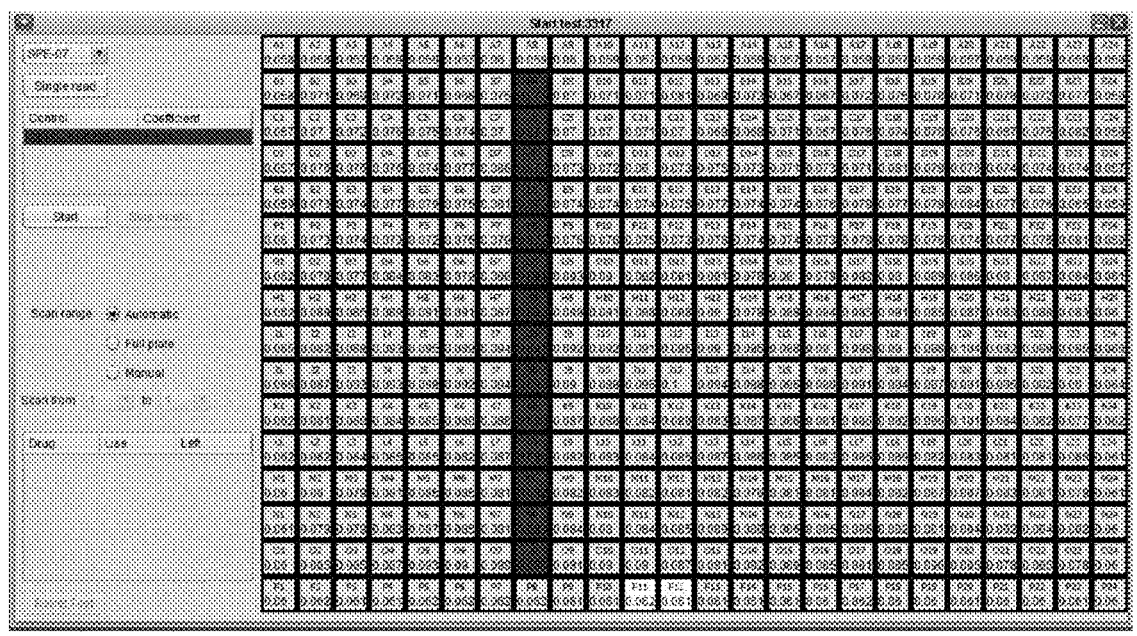

If the single read proceeds correctly, the control wells will be highlighted as shown in FIG. 24, and the coefficient will appear in the upper table. If the coefficient is not within the acceptable limit, a warning message will appear. To insure that the plate is placed in the correct orientation, well A1 will be tested. Every patient or cell line test requires that well A1 is filled with 17.5 µl of medium+2.5 υl of trypan blue 0.1% (1:4) dilution of the stock bottle.

After the initial reading of the plate, if the returned OD value in well A1 is not above 1.2, a warning message will ask for verification of the plate orientation. Once proper orientation is established, the Start button can be unlocked by entering the password of the currently logged in user and pressing OK. The scan range can be adjusted by selecting one of the three options:

Automatic: The scanning range will be determined by the software.

Full plate: The entire plate will be scanned.

Manual: The user can select a specific scanning range.

The Drug table at the bottom left of FIG. 24 is used to adjust the drug inventory. Each drug included in the template will show up in this table (except for fresh drugs). The number of aliquots used to prepare the plate can be adjusted, and this quantity will be automatically reduced from the inventory. If an aliquot was used to prepare more than one plate, the user indicates 1 for the first test that is started and sets 0 for the subsequent tests.

After all of the foregoing parameters have been defined, the test is started by selecting the Start button. The interface will be frozen until the first read is completed, and the window can then be closed. The Start button changes into a Pause button that can be used to pause a test. When a test is paused, a timer will appear to show the duration of the pause, and a Restart button appears. In most cases, a pause should not last beyond 15 minutes. To restart the test, the user selects the Restart button. At all times, the test can be stopped by clicking on the Stop button. When a test is stopped, a pop up window will appear asking the user if the state of the test should be set as Complete. Selection of Yes will categorize the test as Complete, while selecting No will categorize the test as Incomplete.

The Reset Test button below the drug list in FIG. 24 is used to erase all the accumulated data without deleting the test itself. This option cannot be undone, and this feature is disabled if more than six reads were performed. From this point, the kinetic measurements must be stopped and a new test must be created.

Displaying Test Results

Figure 25:
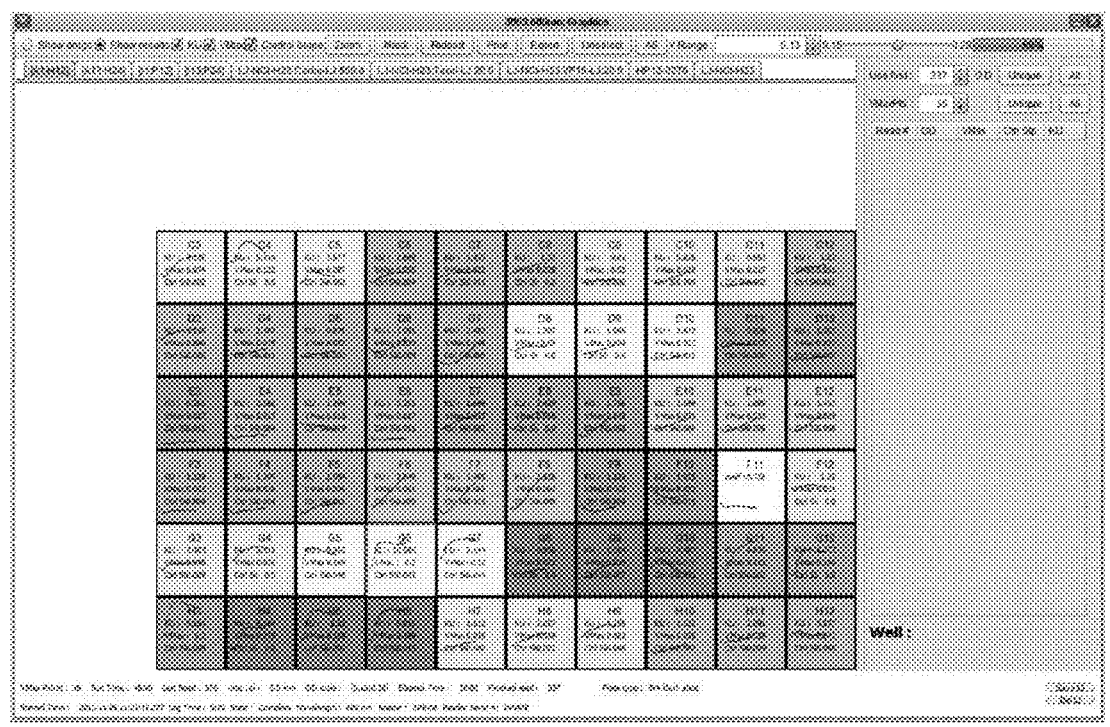

Once a test has been performed, the results of the test are displayed in an interface similar to that shown in FIG. 25. If the test is performed in a 384-well plate, the user can navigate through the four quadrants of the plate by using tabs above the virtual well plate. All the test parameters are included in the status bar located beneath the virtual well plate. Selectable options for the user which affect the display of results are described below:

Show drugs: Displays the drugs assigned to every well instead of the calculated results.

Show results: Displays the calculated results, the KU, the VMax, and the slope of the control at point VMax. The control well will display the value of the coefficient instead of the KU value.

Figure 26:
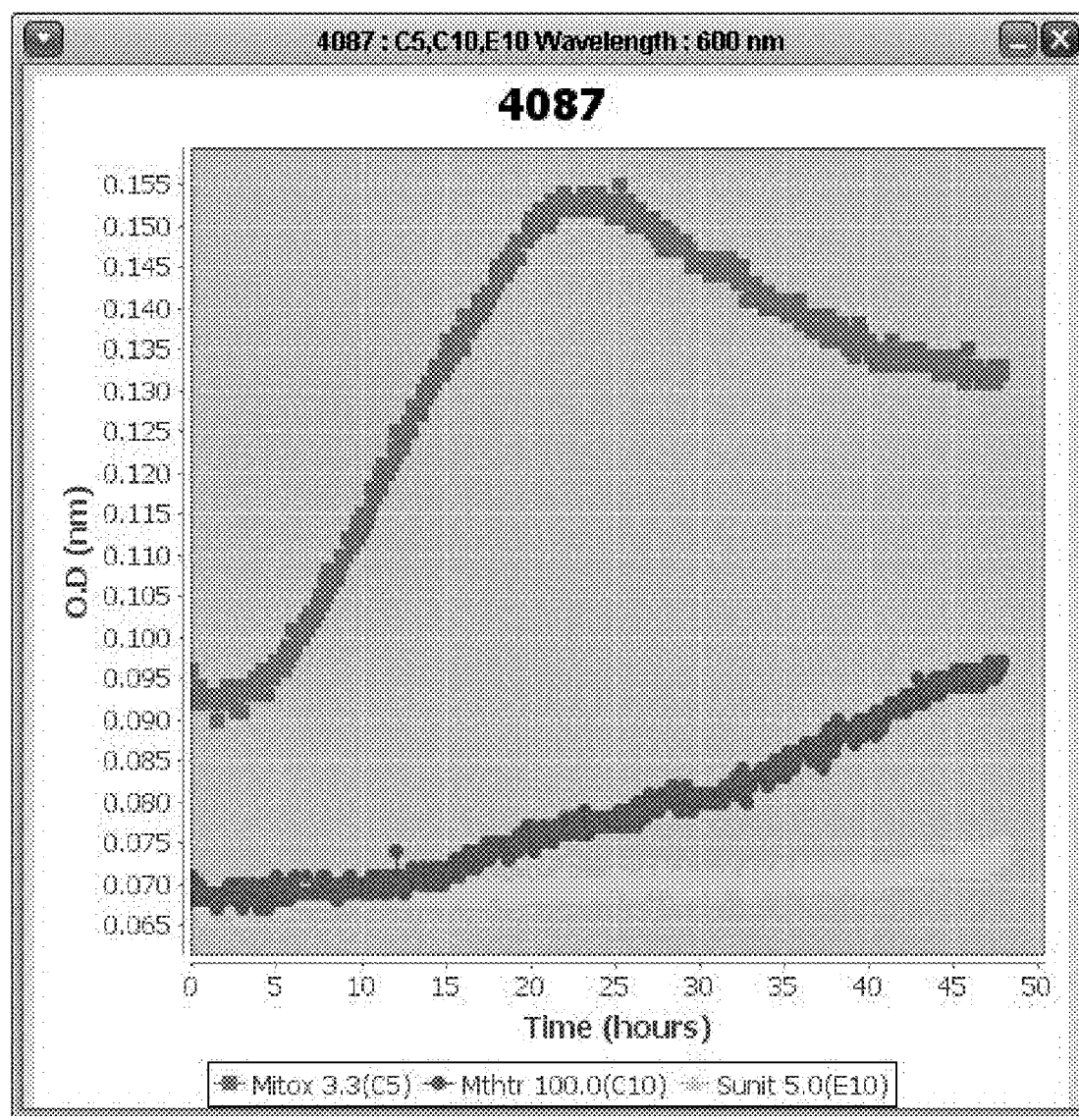

Zoom: Used to zoom into a curve. A graph must first be indicated by selecting one or more wells in the virtual well plate. Multiple curves can be zoomed in the same graph, as shown in FIG. 26, which displays three resulting OD curves from a test.

Mask: To mask a well, the user selects the well, and then selects the Mask button. A masked well will be ignored during the building of the reports. To unmask a well, select a previously masked well, and then select the Mask button. A masked well will appear transparent.

Reload: Will re-perform all the calculations without having to close and reopen the results display. If parameters are changed, the data must be reloaded for the change to take effect.

Print: Produces a ready to print PDF file of the results.

Export: Copy all the KUs in a .txt file.

Unselect: Unselects every selected well.

AS: Auto-Scale, which will adjust the scale so that the entirety of all curves will be visible.

Other options allow for adjusting the Y scale in the curve graphics, wherein the Y Range represents the distance between the lowest and the highest value to be displayed in the graphs, and all the graphs will follow the same scale. A progress bar is also displayed to indicate the progression of the kinetic.

Raw OD, read sequence, and related data of a specific well can be displayed by holding the Ctrl key on the keyboard and selecting on the desired well. The data appears on the right side of FIG. 25, but a more detailed view of the data is shown in FIG. 27. This table contains all the details of the KU's calculations. The highlighted row indicates the position of the VMax, which is the point where the KU is calculated and reported in the results.

It is possible to force the calculation to stop after a certain reading number by inputting a lower value in the Use First box of FIG. 27, which will ignore a portion of the curve. The Unique button will limit the restriction only in the selected well, while the All button will apply the restriction in every well. The portion of the curve that is not used in the calculation will be conspicuously shown in the graphic. To assign a specific VMax, the user can change the value in the VMaxPts field and select the Unique button to assign this VMax to the highlighted well, or select the All button to assign it to all wells in the test. The Coefficient Adjustment Factor box is used to adjust the current coefficient, and the current coefficient will be multiplied by the value in this field.

Importantly, if a Levey-Jennings (LJ) cell line was assigned to the test, additional buttons will appear to allow the user the following options. The Save LJ button (shown in FIG. 25) will allow the user to save all unmasked KU (assigned to LJ cell line) in the cumulative Levey Jennings database. These KU will be included in the overall mean and standard deviation used to compare previous and other assays. The Del q button (shown in FIG. 25) will allows the user to remove all the KU included in this test from the cumulative Levey Jennings database. The overall mean and standard deviation will be updated to remove these values. Deleted values can be added back in the database by selecting the Save LJ button.

Figure 28:
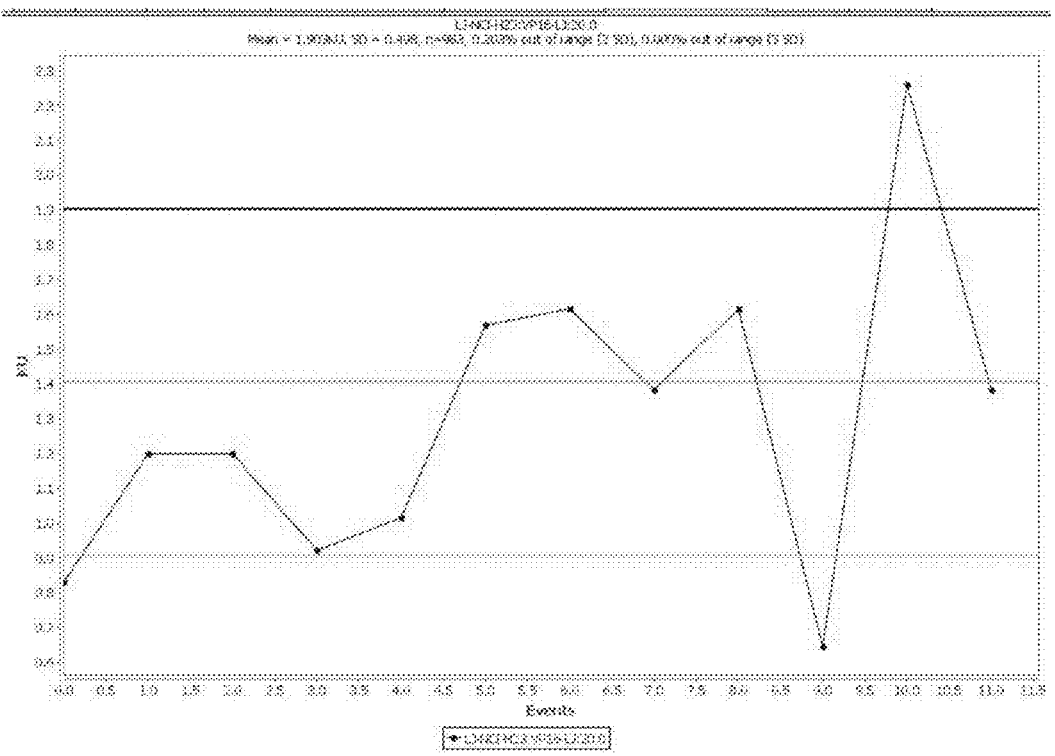

Saving the KU to the Levey-Jennings database or opening the results of a test with KU that were already saved in the database will cause new tabs to appear next to the plate quadrant tabs, also shown in FIG. 25. Selection of these tabs will show the Levey-Jennings plot associated with the chosen drugs with an LJ extension, similar to that shown in FIG. 28. The mean and standard deviation are calculated using all the KU previously saved to the Levey Jennings database. On the plot shown in FIG. 28, one line represents the average, while others represents respectively 1SD, 2SD and 3SD. All statistics are calculated from the accumulated data.

Managing Projects

Figure 29:
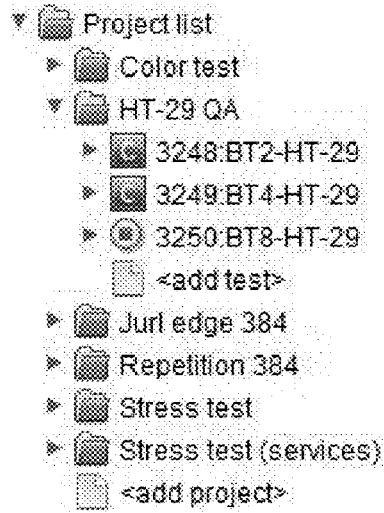

The PROJECT tab and its selection options are shown in FIG. 29, and are similar to the TESTS tab. This allows the user to categorize tests, making them easier to find. To open a project, the user selects the project name. To create a new project, the user selects the <add project> option, types the project name, and selects OK.

To add a test to a project, the user selects the project name to expand the tree and then selects the <add test> option. An interface containing all existing tests ID will appear. The user selects the desired test, and then selects the <add existing> option. It is also possible to create a new test. Also, a test can be included in more than one project.

To remove a test from a project, the user selects the test and uses the Delete key on the keyboard. The test will be removed from the project, but it will still be available in the TESTS tab. Likewise, to delete a project, the user selects the project name and uses the Delete key on the keyboard.

Managing Patients

Figure 30:
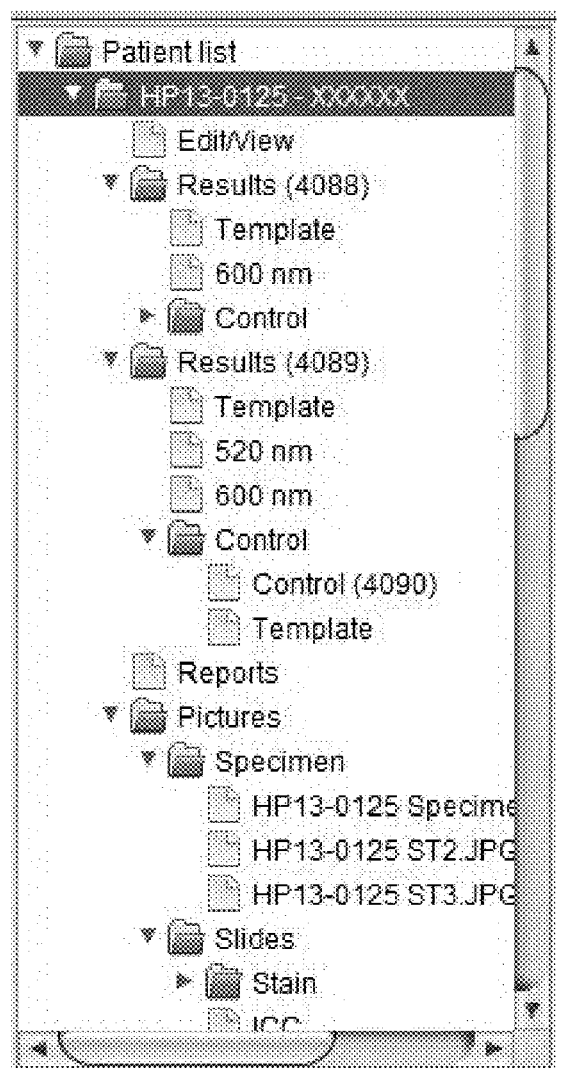

The PATIENTS tab is used to display all the patients' related information in OPIE. Navigation is similar to the TESTS tab, and includes the following selectable options which can be expanded as described herein, as shown in FIG. 30.

Edit/View: This is the same as editing a cell line in the TESTS tab.

Results (includes a test number): Views the results (see the Results section of the TESTS tabs section) of the tests number included. One node will be created for every test that this specimen is assigned to. If a control cell test was assigned to this test number, the control test's numbers will appear under the Control folder.

Reports: Views this patient report. Only the medical director, or others with suitably high credentials, can edit the report. Other users with lower credentials are limited to view and fax history.

Pictures: View/upload all the pictures assigned to this patient. To view a picture, the user selects the picture name.

Figure 31:
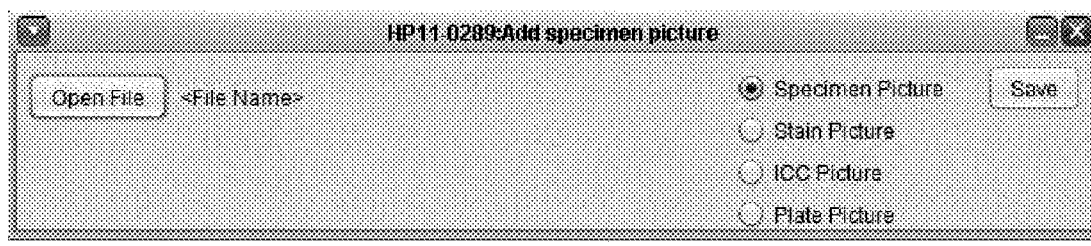

To add pictures, the user selects the <add picture> option, and the interface of FIG. 31 will appear. The Open File button is used to select the pictures that needs to be uploaded. Multiple files can be selected by holding down the Ctrl key on most computers. Care should be taken to select only pictures that are in the same category, i.e. do not select ICC and plate pictures at the same time. When the pictures are opened, the user selects the picture category and selects the Save button. The picture name will appear in the node that corresponds to the category that was selected before clicking the Save button. Pictures are deleted by selecting the picture in the tree and using the Delete key on the keyboard.

Reports are filed under the Reports folder, which can be expanded to see all the reports that are associated with the patient. If no report were written for this patient, only the <add report> node will appears, otherwise a concatenation of tests numbers will appear. This concatenation is the report ID, and it is composed of all the test ID's that were used to create this report. The No Data node will appear if a report was created without using the data from a test.

Figure 32:
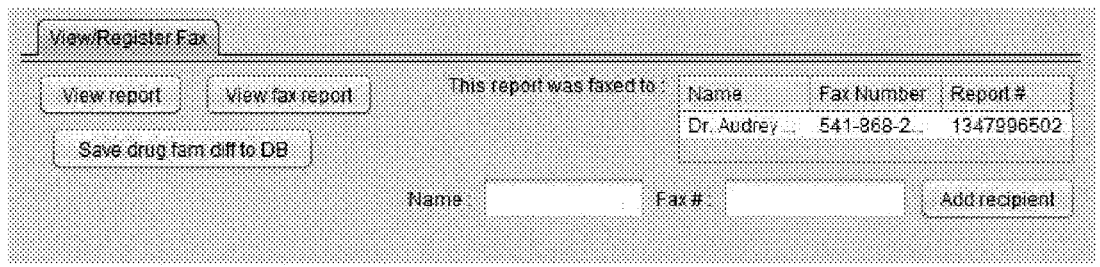

To display the data associated with a report, the user selects the report ID and the interface of FIG. 32 will appear. To view the report, the user selects the View Report button. To view a report with a black and white table suitable for facsimile transmission, the user selects View Fax Report. If the report was faxed, the recipient name and fax number are shown in the appropriate text fields, and additional recipients can be added by selecting Add Recipient. Once this is performed, the report is marked as completed and cannot be edited any further. From this point, the medical director or similar official will be required to create an addendum report.

Figure 33:
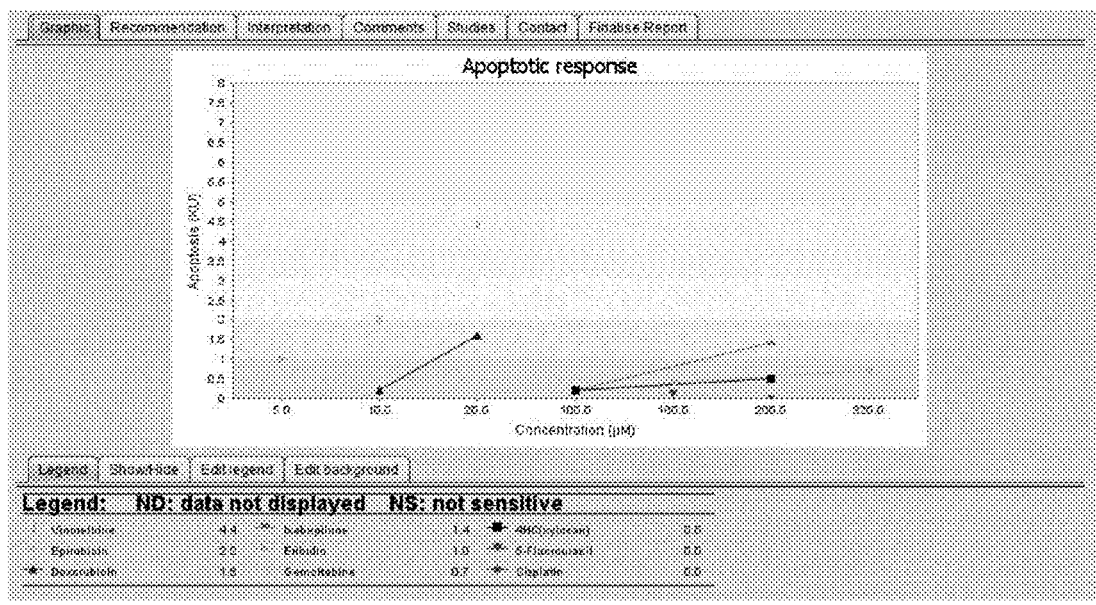

If the user's login credentials allow him to create reports, the interface of FIG. 33 appears instead of the interface of FIG. 32. The tabs at the top of the interface are used to navigate among all the report's sections. The Graphic tab is used to build the graphic that will appear in the report. In this section, it is possible to remove a series from the graphic and the legend, and edit the Y range and the markers. The Show/Hide tab below the graph is used to remove a series from the graphic. To do so, the user selects the series' name desired for removal from the graphic. A removed series will be listed as ND (data not displayed) in the legend.

Figure 34:
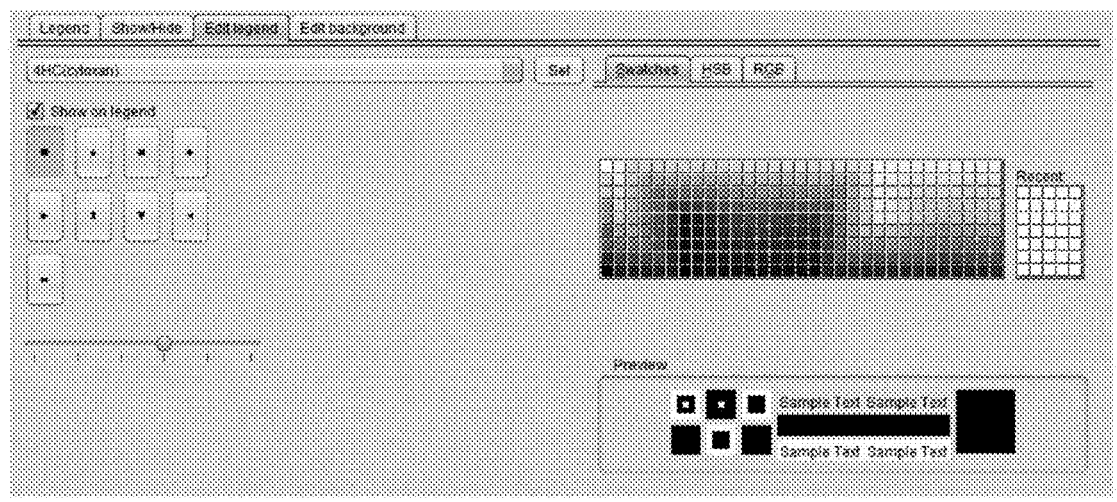

The Edit Legend tab below the graphic of FIG. 33 is used to remove a series from the legend and to edit the markers, which expands to provide the options shown in FIG. 34. To edit a series, the user selects the series' name from the list, picks the desired shape, adjusts the slider to change the size of the markers in the graphic, and picks a color. The Set button is selected to save the modification before selecting another series. The Show On Legend check box is used to remove or display the series on the legend. The Edit Background tab in FIG. 34 is used to adjust the range of the Y axis, the size of the sections, the color of the sections, and the shape of the series.

Figures 35, 36:
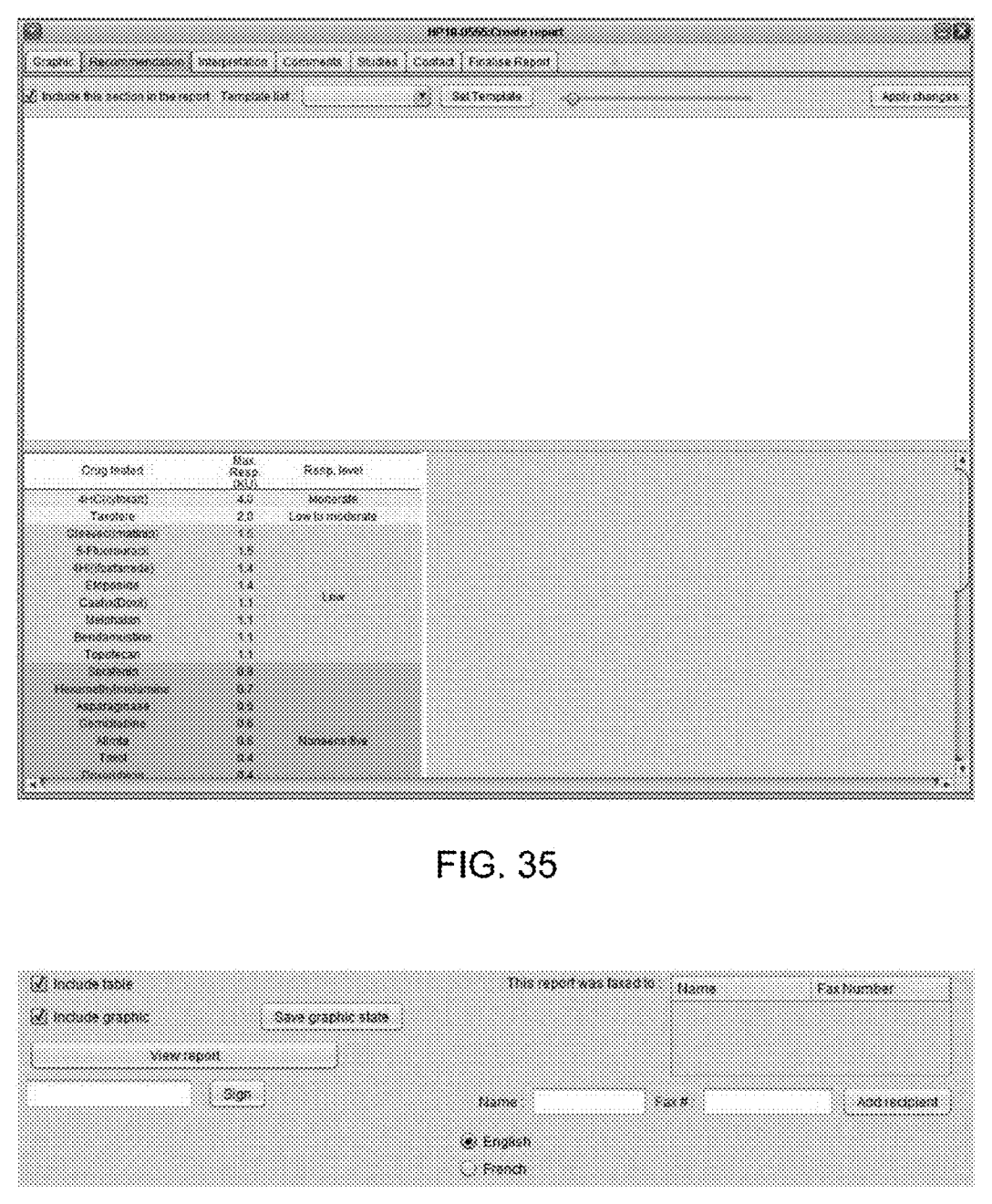

Returning to FIG. 32, the Recommendation tab can be expanded to display the interface of FIG. 35, which is also used by the remaining tabs, namely Interpretation, Comments, Studies, Contact, and Finalize Report. The upper section (text area) is used to type the text to be included in the drug selection section of the report, and the lower section shows the table that will be included in the report. Various additional options allows the user to control the content and format of the report.

This Finalize Report tab interface of FIG. 36 is similar to the View/Register Fax interface described above with respect to FIG. 32, and the data fields shared between the two interfaces serve the same purpose.

Finally, if the report is marked as complete and a user desires to edit this report, a message interface will ask if the user wants to create an addendum report. If No is selected, the report editing interface will appear, but every section will be locked, except the Finalize report section. If Yes is selected, a new report editing interface will appear. The produced report will then contain an addendum section that can be edited the same as the other text sections. An addendum report will have the addendum number in the report ID.

Other Settings and Information

Figure 37:
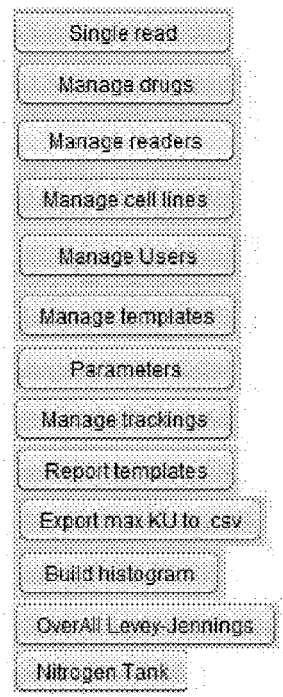

The OTHERS tab of the OPIE system contains complementary modules and managements modules. When the user selects the OTHERS tab, the panel displays the options shown in FIG. 37.

Figure 38:
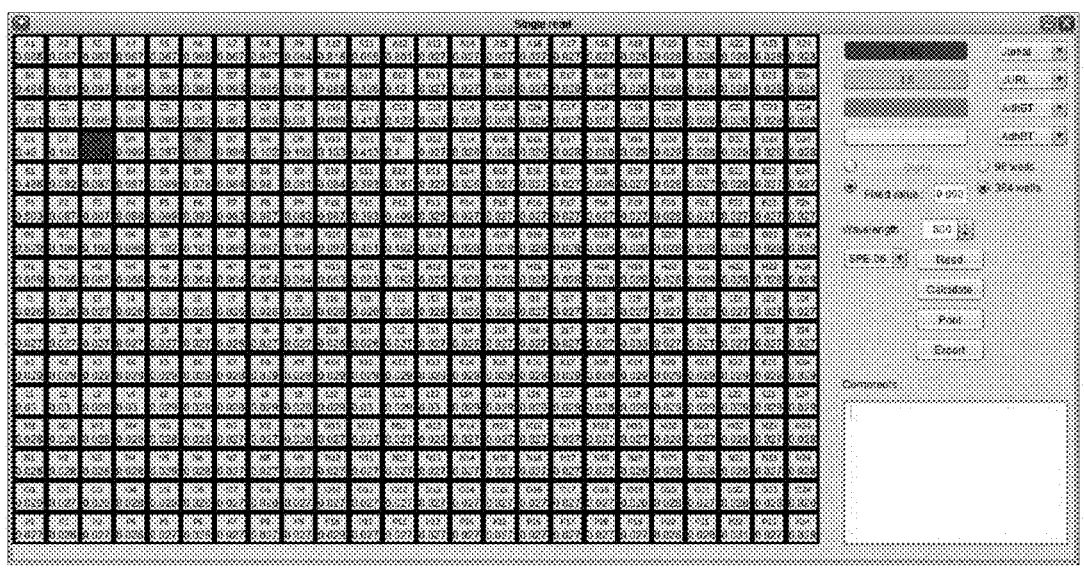
Figure 39:
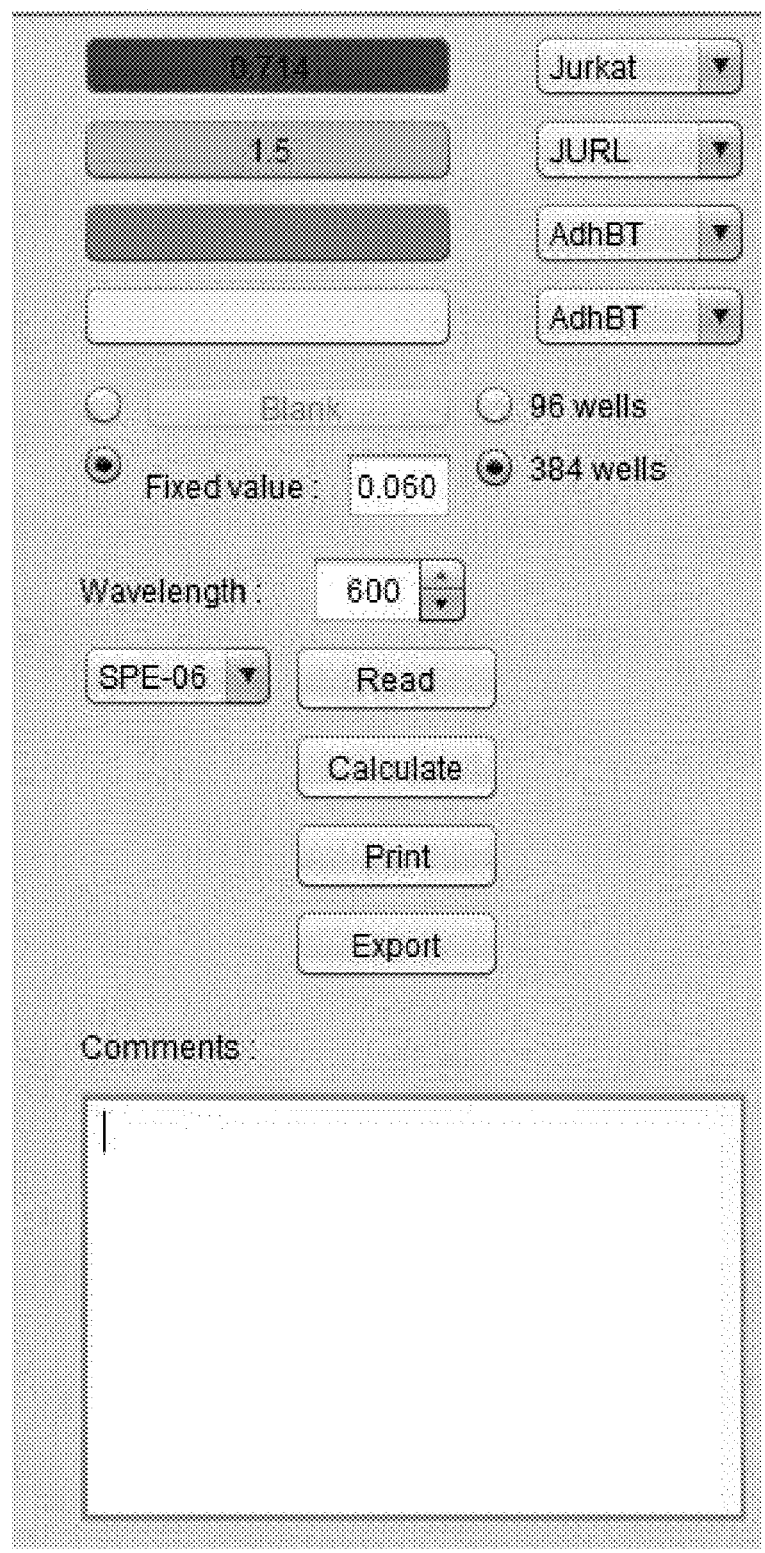

The Single Read module is used to perform a single read of a plate and perform a coefficient calculation. To perform a single read, the user selects the Single Read button and the interface of FIG. 38 will appear. The left section contains the virtual well table that will display all the ODs, and the right section, shown more clearly in FIG. 39, contains the interface to perform a single read and coefficient calculation. With reference to FIG. 39, this upper portion of the interface is used to select the cell line and to pick the wells that contain the appropriate cell lines. To set up a well, the corresponding colored button is selected, and then the user selects inside the well. The blanks are associated the same way that the cell line are. If the plate does not contain any blanks a fixed value can be assigned. The well plate type (96 or 384) and wavelength must be selected before reading the plate. To read the plate, the user selects the Read button. To perform the coefficient calculation, the user selects the Calculate button, which can be done multiple time per read (the well assignations can be changed without having to repeat the reading of the plate). The Export button will create a text file that contains all the ODs. The Print button will print the virtual well table along with the calculated coefficient and the comments that were typed in the Comments text area.

The Manage Drugs module is used to manage the drug inventory and to visualize the drugs preparation forms. The OPIE system automatically manages the drug inventory. For example, when a test is started, the inventory will be automatically updated. Selection of the Manage Drugs button displays the interface of FIG. 40. Drugs can be added, saved, and deleted in a manner that will be familiar to persons using similar interfaces. Care must be taken to verify that the dilution expiration date does not exceed the stock expiration date. The user can navigate through the inventory using the directional buttons located in the upper icon bar. The drugs that are listed in the templates are directly linked with the drugs listed in the inventory.

If desired, the user can show only drugs that are set to expire within a selected time range using the calendar icon, while the box next to the calendar icon is used to adjust the time range. To include stocks expiration, the user can select the Stock check box, and to include dilutions, the Dilution check box. The Aliquots Left box is used to include drugs that have less than a certain number of aliquots left, which setting (minimum number of aliquots left) can be selected by the user. The Prepare Fresh check box is used to indicate that this drug must be prepared fresh, and selecting this check box will remove the fields that are associated with dilutions (the right column). Drugs that are marked as "research and development" (R&D) will not appear when the Show Expired Drugs button is used via the calendar icon.

Selection of the Color May Interfere check box indicates that this drug is a colored drug whose properties could interfere with the spectrophotometer's OD measurement. A warning box will appear to the user when starting a test with a template that includes a drug marked as a "colored" drug in this manner.

To upload a dilution preparation form, the user selects the Save Form button, and the previously uploaded form will be overwritten. To view a dilution preparation form, the user selects the View Form button.

Figure 40:
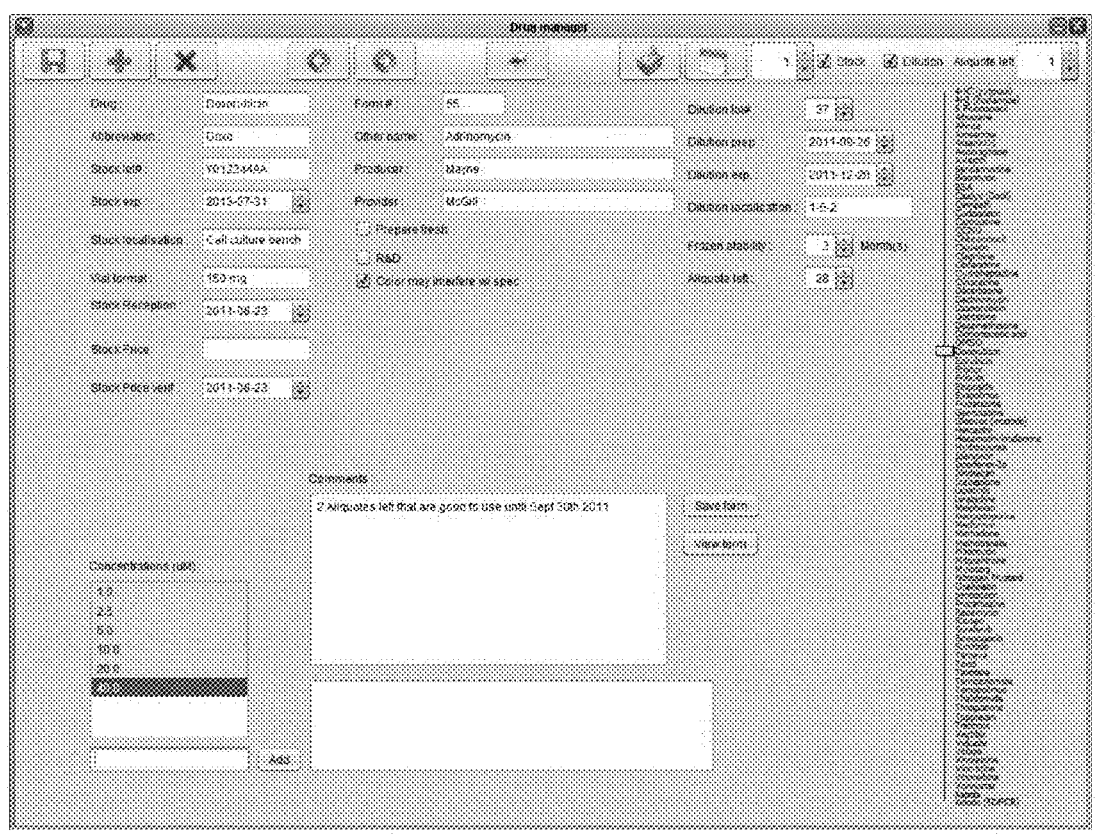

The Concentrations table at the bottom left of FIG. 40 lists all the possible aliquot concentrations for this drug. The concentration list in the template editor is directly linked to this list. To add a concentration, the user types the value in the text field and selects the Add button. To remove a concentration, the user selects the concentration in the list and uses the Delete key on the keyboard.

Figures 41, 42:
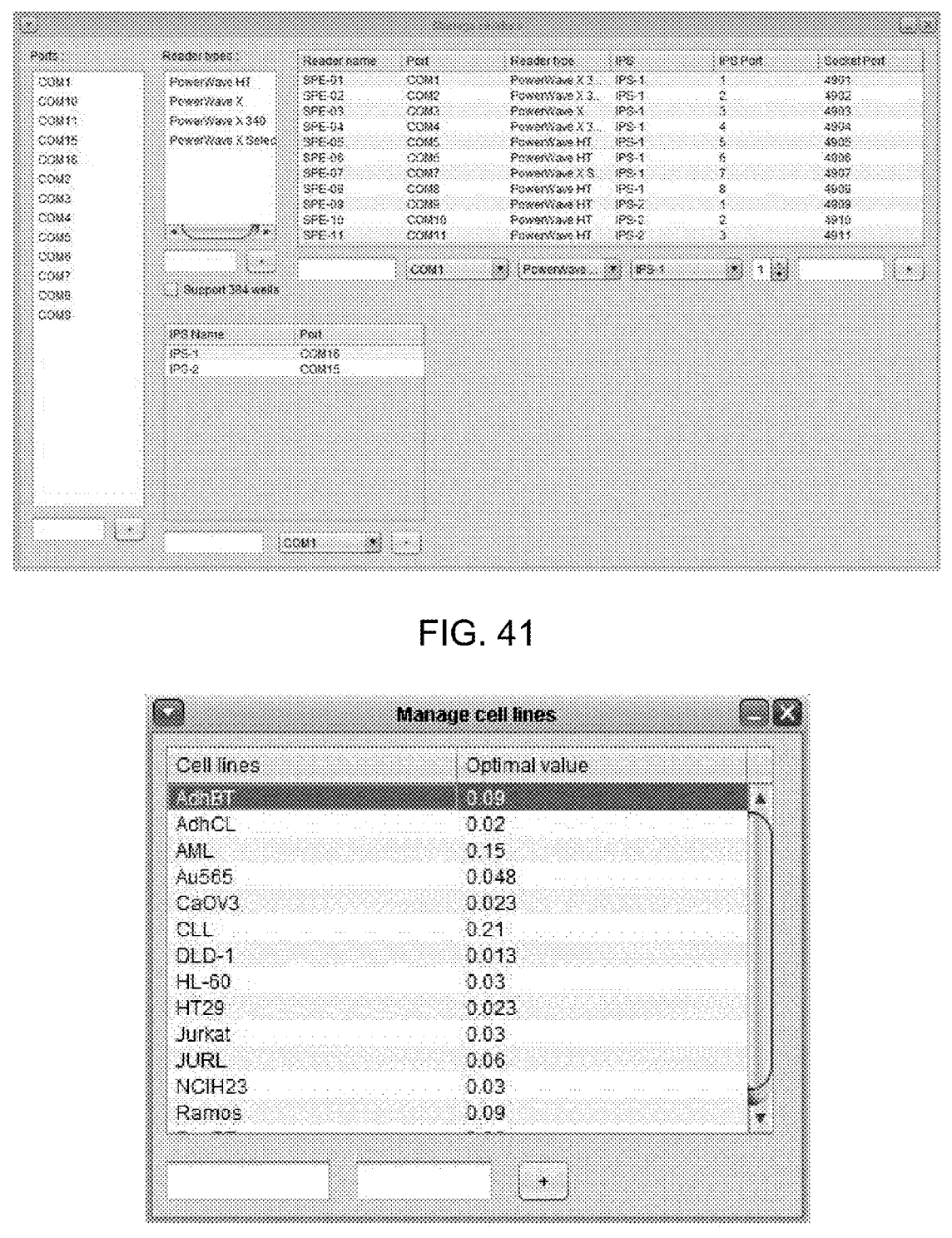

The Manage Reader module is used to setup the readers, which includes their physical connection to the server and the IPS and their logical name that appears within the OPIE system. Access to the Manage Reader module can be restricted to managers and others with suitably high login credentials. When the user selects the Manage Reader button, the interface of FIG. 41 is displayed, and readers are added to OPIE using the following steps:

Create a Port. A Port represents the physical connection to the server. To create a Port, the user enters the port name in the text field under the port list, and the user selects the + button. To see a list of available ports and port names on the server, the Device Manager on the server is selected and the port node is expanded. The port name in OPIE must match the name listed in the Device Manager.

Create an IPS (Internet Power Switch). The user enters the IPS name in the text field under the IPS list and then selects a port. The port must match the port used to connect the IPS to the server.

Create or select a reader type. The user enters the reader type in the text field under the Reader Types list and checks the Support 384 Wells check box if the reader can read a 384 well plate. This will ensure that only readers that support 384 well plates will be available when a user tries to start a test that uses the larger well plate.

Create a logical reader name. The user enters the reader logical name in the text field under the reader table, which is the name that will appear in the reader list in the Start Test and Single Read interfaces. The user then selects the port that corresponds to the server port where the reader is connected to the server. The corresponding reader type is selected, along with the IPS where the reader is connected and the outlet number on the IPS where the reader is plugged. Lastly, the user enters the socket port number in the last text field, as each reader must have its own unique socket number. The available socket port numbers are within the range of 4900 to 4999. The user selects the + button to add the reader to the table. The reader table can be edited by selecting the field that requires modification. Physical ports can only be associated with one device, so attention must be paid to verify that each port is only used one time.

The Manage Cell Lines module, displayed as the interface of FIG. 42, is used to edit, create, and delete cell lines, and is also used to set the optimal value for the coefficient calculation using the following formula:

$$\text{Coefficient} = X/(\text{Average OD}_{ctrl} - \text{Average OD}_{blnk})$$

where X=optimal value.

To create a new cell line, the user enters the name of the cell line and the optimal value in the text fields under the table, and then selects the + button. The optimal value can be changed by selecting the value in the table. Cell lines cannot be renamed, but must be deleted and recreated. Importantly, deleting a cell line will break the calculation in every test that uses the deleted cell line.

Figure 43:
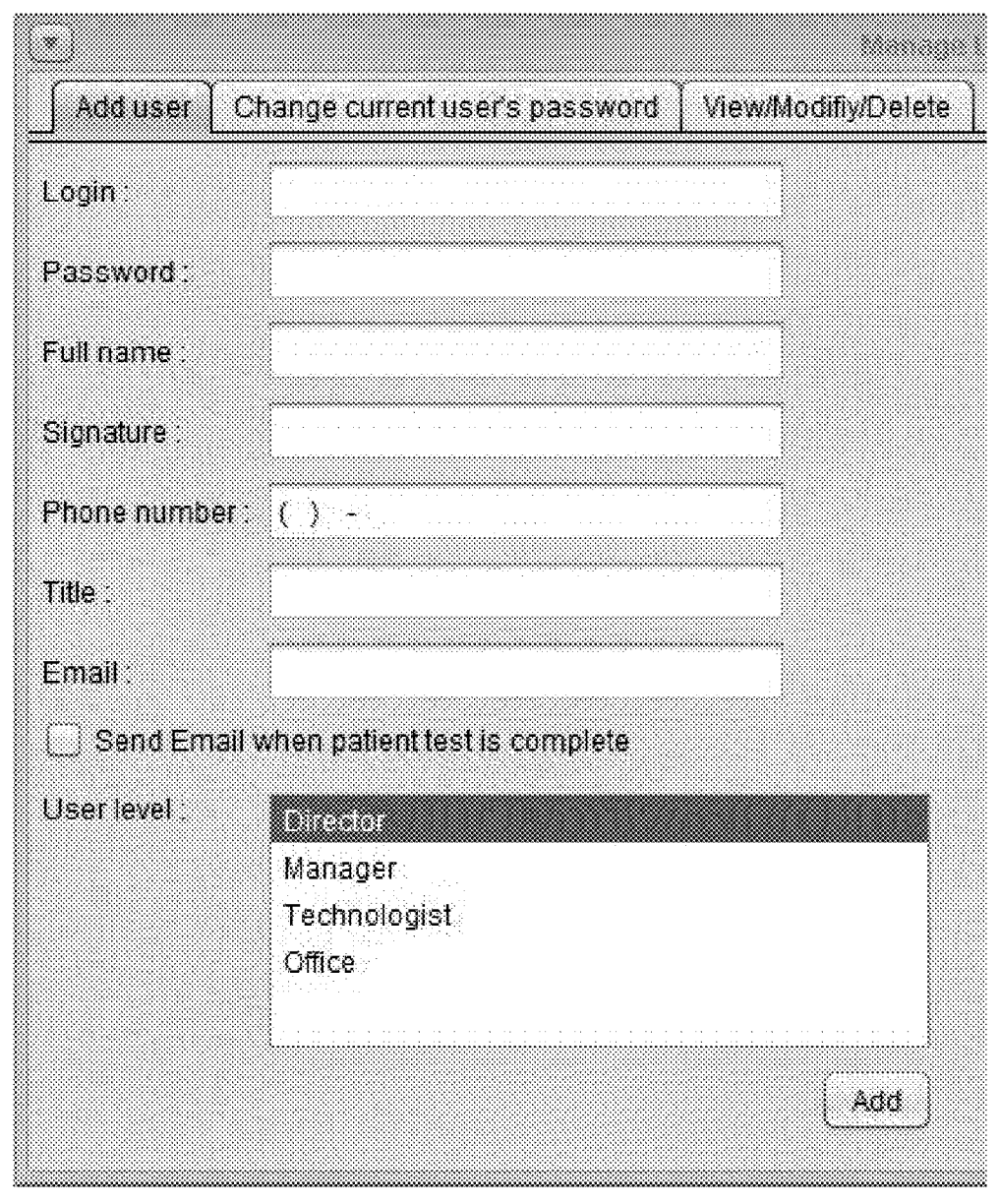

The Manage Users module is used to edit, create, and delete users, and it displays an interface shown in FIG. 43. The Change Current User's Password tab can be used by any user to change his password. To change a password, the user enters the old password followed by the new password and selects the OK button. The View/Modify/Delete tab contains a table with all the users' descriptions. To modify a user's parameters, the user selects the field to modify and enters the new value. Deleting a user is performed by selecting the user's name and using the Delete key on the keyboard. The Add User tab is used to create a new user with data fields commonly employed in similar situations, including access level for verifying authentication credentials at login.

The Manage Templates module is used to create or edit pre-defined templates. The interface is the same as the test template editor of FIG. 19, except for the type assignation (type is left empty).

Figure 44A:
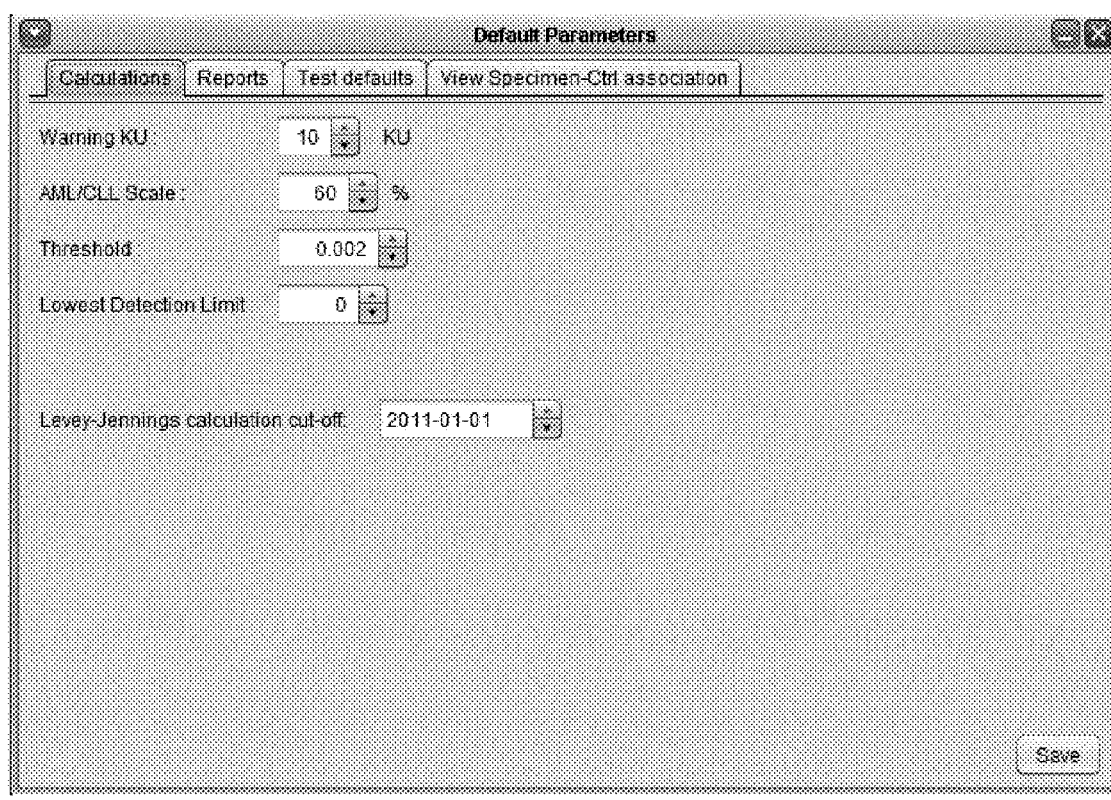
Figure 44B:
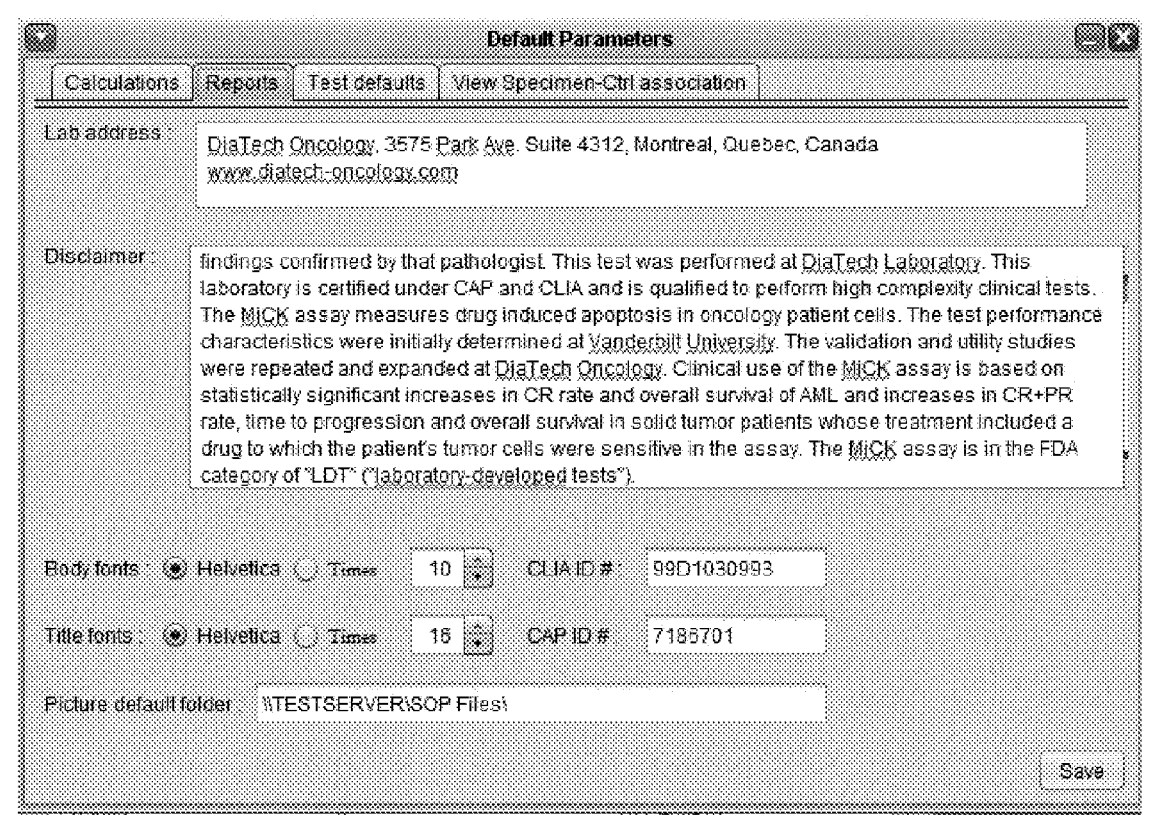
Figure 44C:
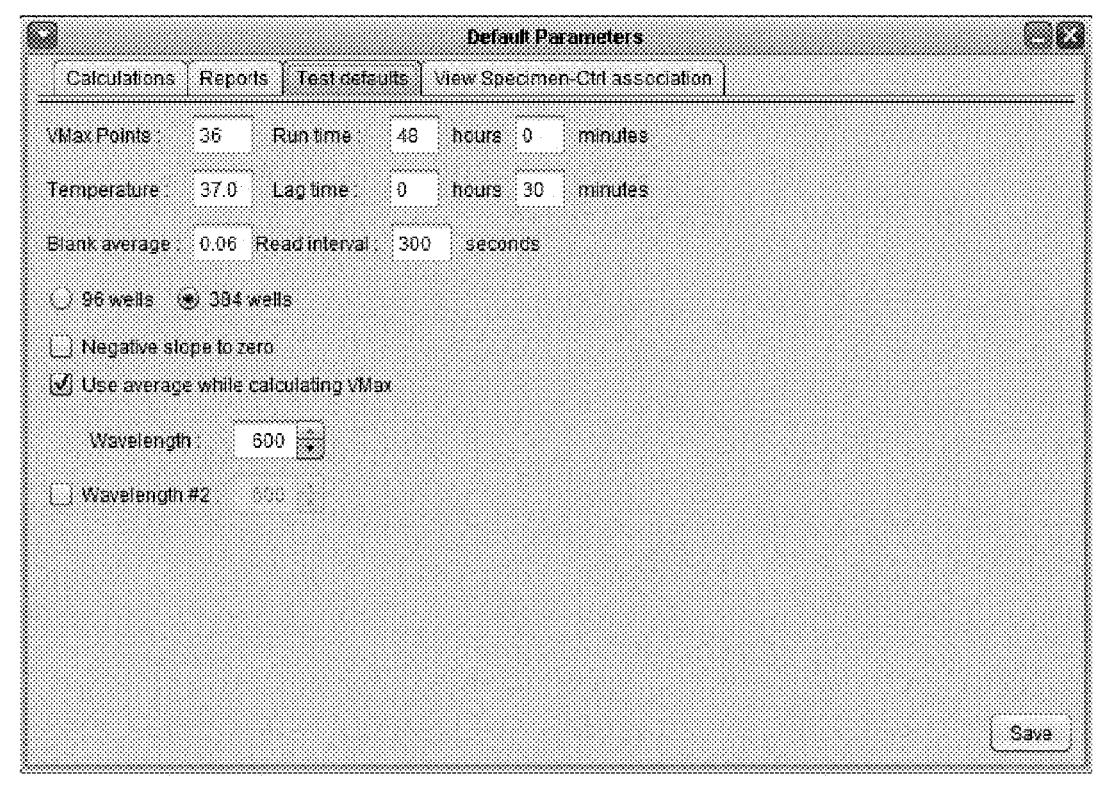

The Parameters module is use to define and edit many of the default OPIE settings, as displayed in the interfaces of FIGS. 44A, 44B, and 44C. The parameters are separated in three categories: Calculations, Reports, and Test Defaults. With respect to Calculations as shown in FIG. 44A, this means parameters that affect how the KUs are calculated, such as:

Warning KU: If a KU is above this value, this KU will appear over a red background in the report editing windows. Generally a KU above this value could be caused by a manipulation error (air bubble, no oil, etc.) during the manipulation of the plate and a visual inspection of the plate should be done to confirm that the value is real.

AML/CLL scale: If a cell line is associated with AML or CLL the final KUs will be multiplied by this parameter.

Threshold: During the calculation of the V MAX, if the two ODs used to calculate the slope do not have a difference higher than the set threshold, the slope will be considered to be null.

Lowest detection limit: Any KUs below this value will be considered as null, and in the reports they will be replaced by NS (not sensitive).

Levey Jennings calculation cut-off: Every Levey-Jennings data that were accumulated before this data will not be considered when calculating statistics and not displayed in the overall plot.

With respect to Reports as shown in FIG. 44B, this means parameters that affect the output of the reports, such as lab address, disclaimers, fonts, default folders for images, and other identifying information.

With respect to Test Defaults as shown in FIG. 44C, this means parameters that are used when a new test is created.

Referring back to FIG. 37 for the remaining modules under the OTHER tab, the Manage Trackings module is used to edit, create, delete, and send specimen collection kits to healthcare providers.

The Report Templates module allows the medical director or similarly credentialed users to edit and create report templates.

The Export Max KU to .csv module allows the user to export files that contain the maximum KU from a list of specimen ID's and drugs.

Figure 45:
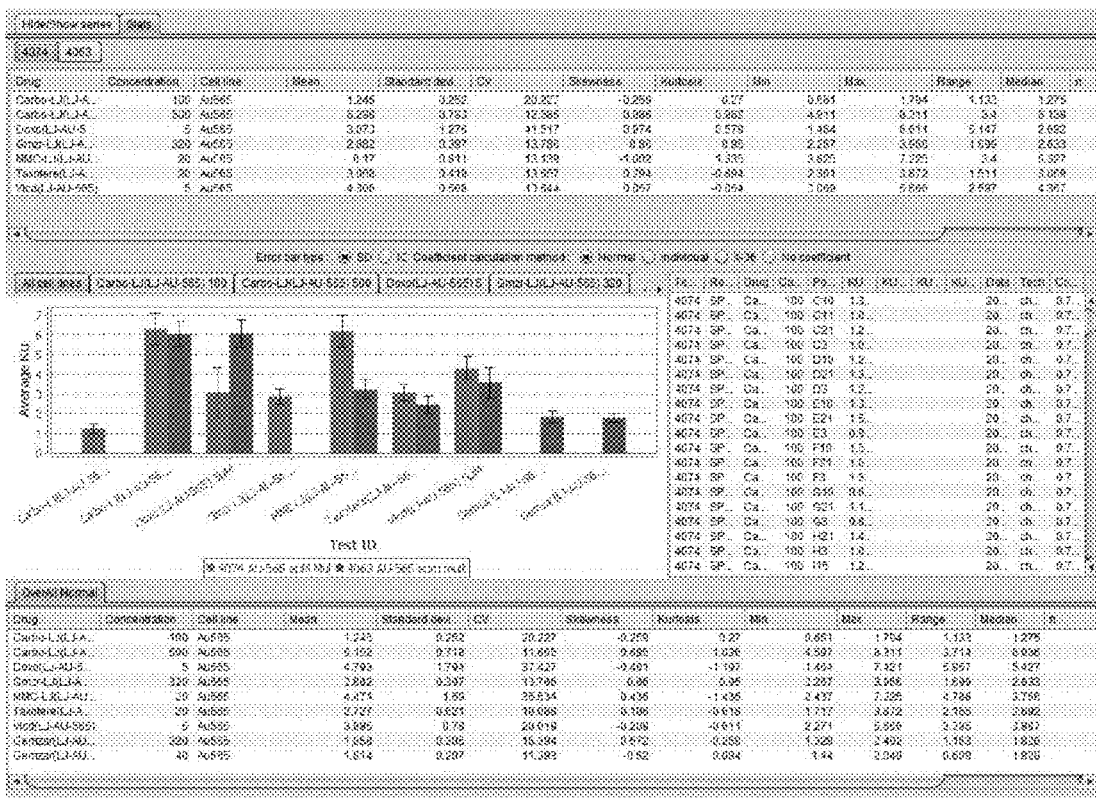

The Build Histogram module allows creation of a histogram of drugs vs. KU for any test combinations, as shown in the interface of FIG. 45. This will also generate basis statistics for the selected tests. The upper table shows all statistics for each individually selected test, while the lower table show statistics of all selected tests treated as a single set. The middle table shows all KU for every well of every selected test. The middle graph is a histogram that display the drugs-concentration vs. average KU for every selected tests, and Levey Jennings plots are constructed for every drug-concentration. These statistics do not use the data from the overall Levey-Jennings.

Figure 46:
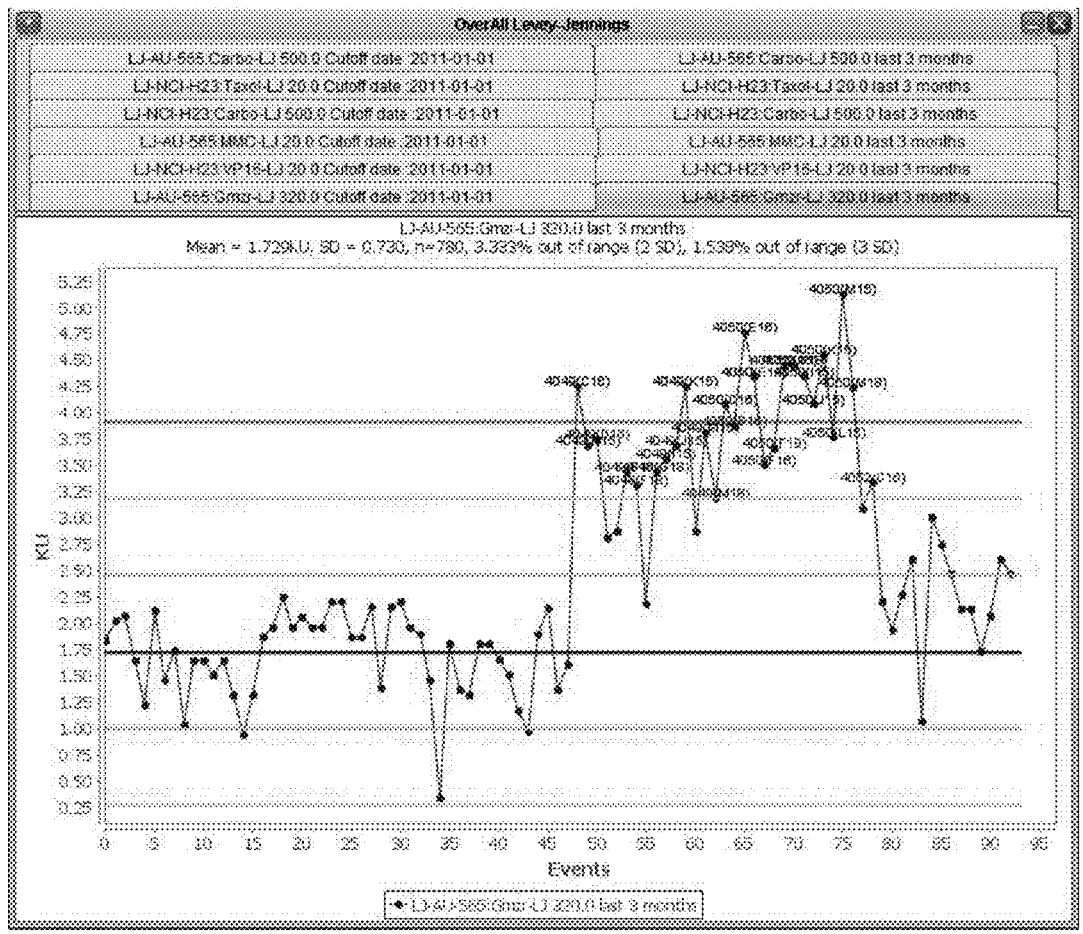

The Overall Levey Jennings module displays all accumulated Levey-Jennings data as shown in the interface of FIG. 46. These plots are standard Levey Jennings (LJ) plots. A plot is generated for all LJ cell line-LJ drugs combination saved in the overall Levey Jennings database. Every point that is out of 2SD has a label with the test ID and well position of the out-of-range value.

The Nitrogen Tank module allows the user to manage all items in nitrogen storage which are used in connection with tests run through the OPIE system.

Figure 47:
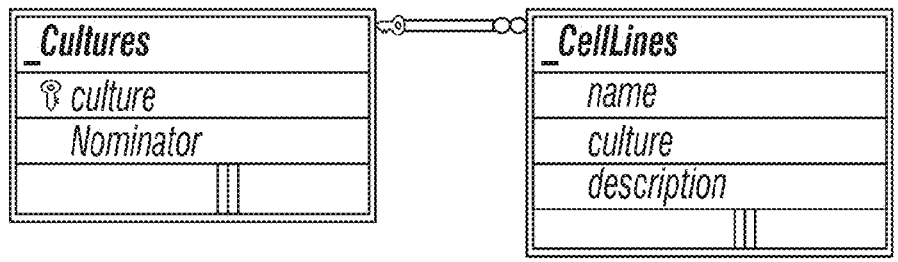
FIG. 47, comprising eight sheets, depicts a preferred embodiment of a relational database structure used in connection with the present invention.
Figure 47:
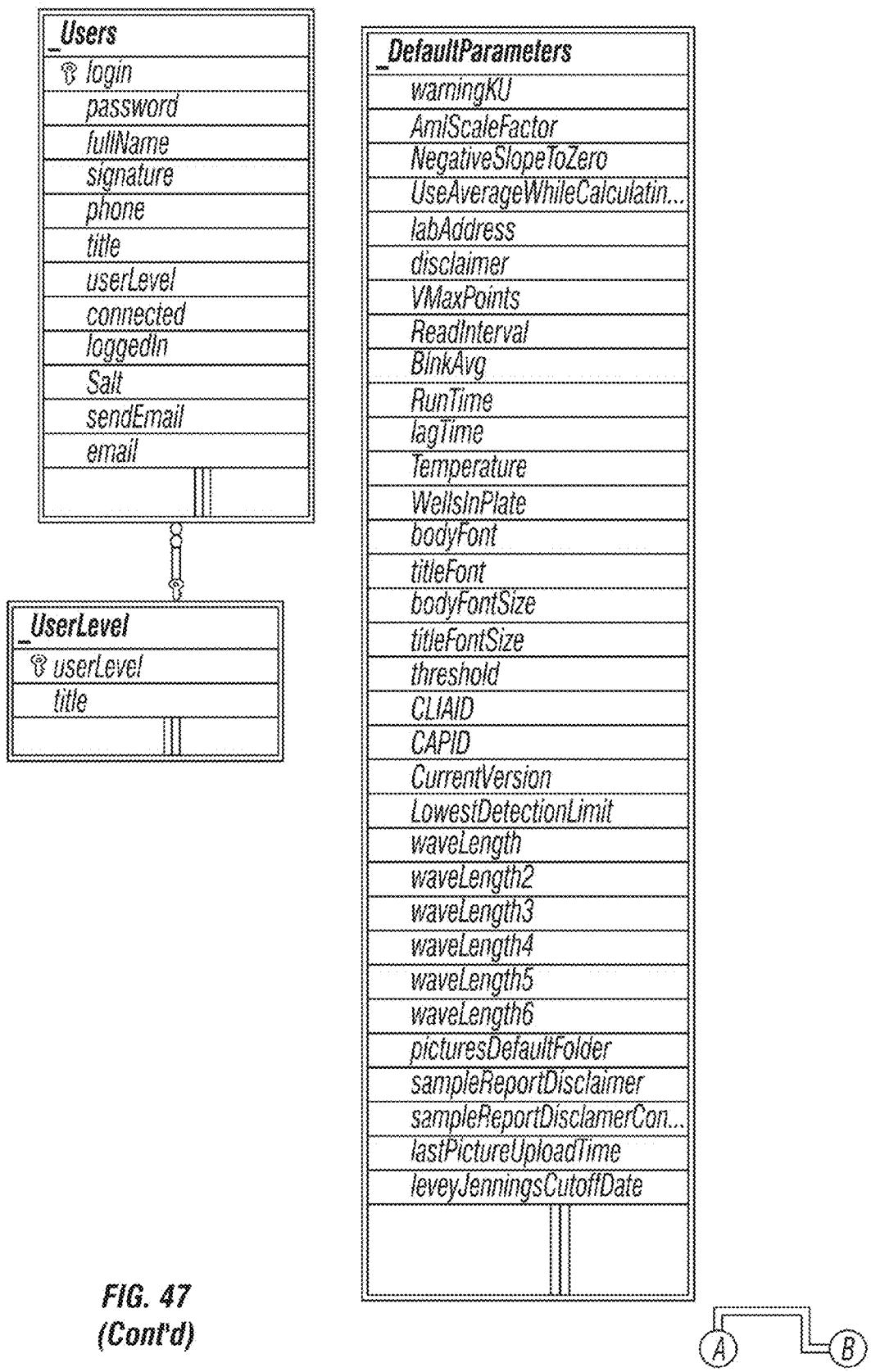
Figure 47:
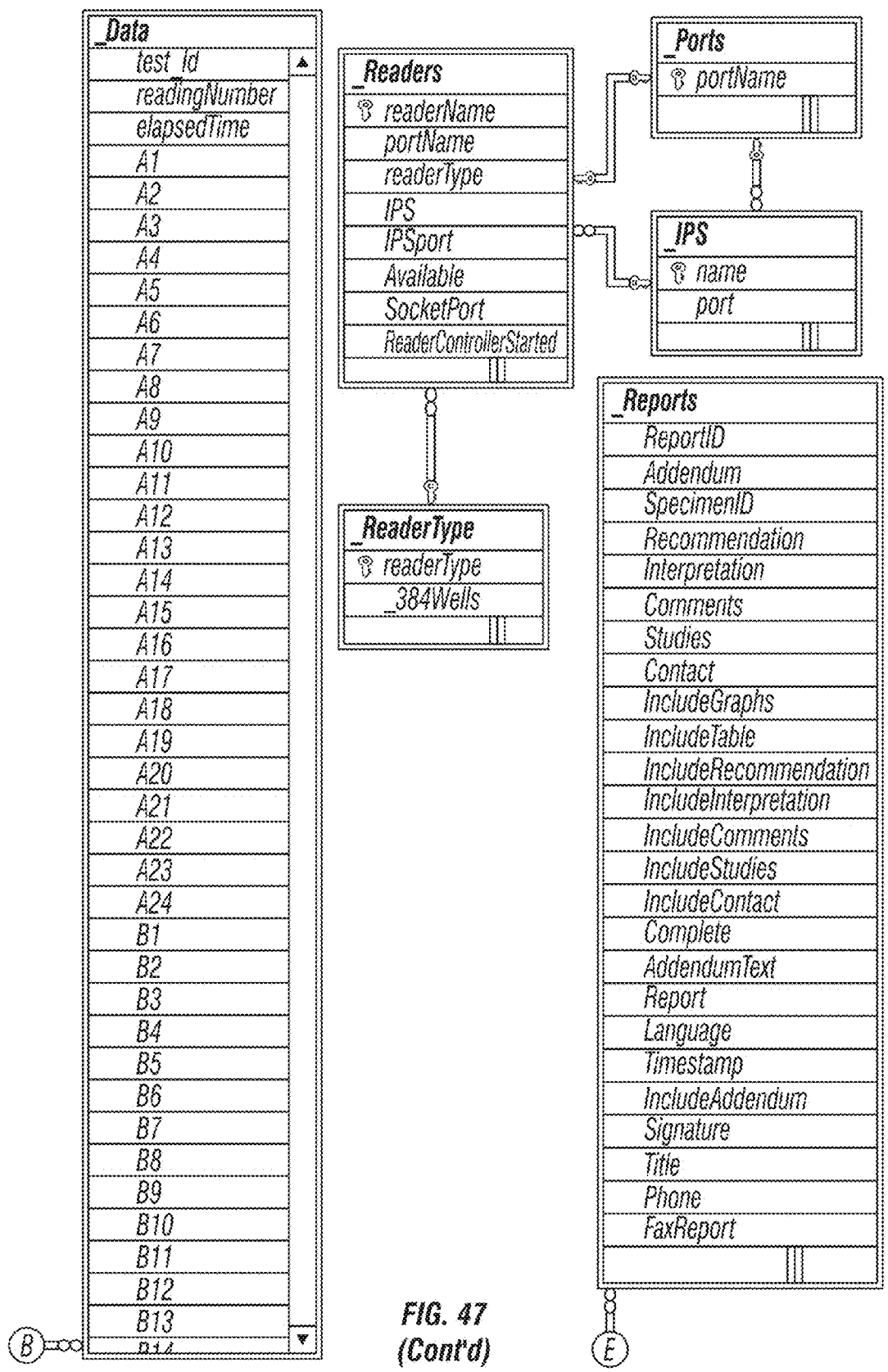
Figure 47:
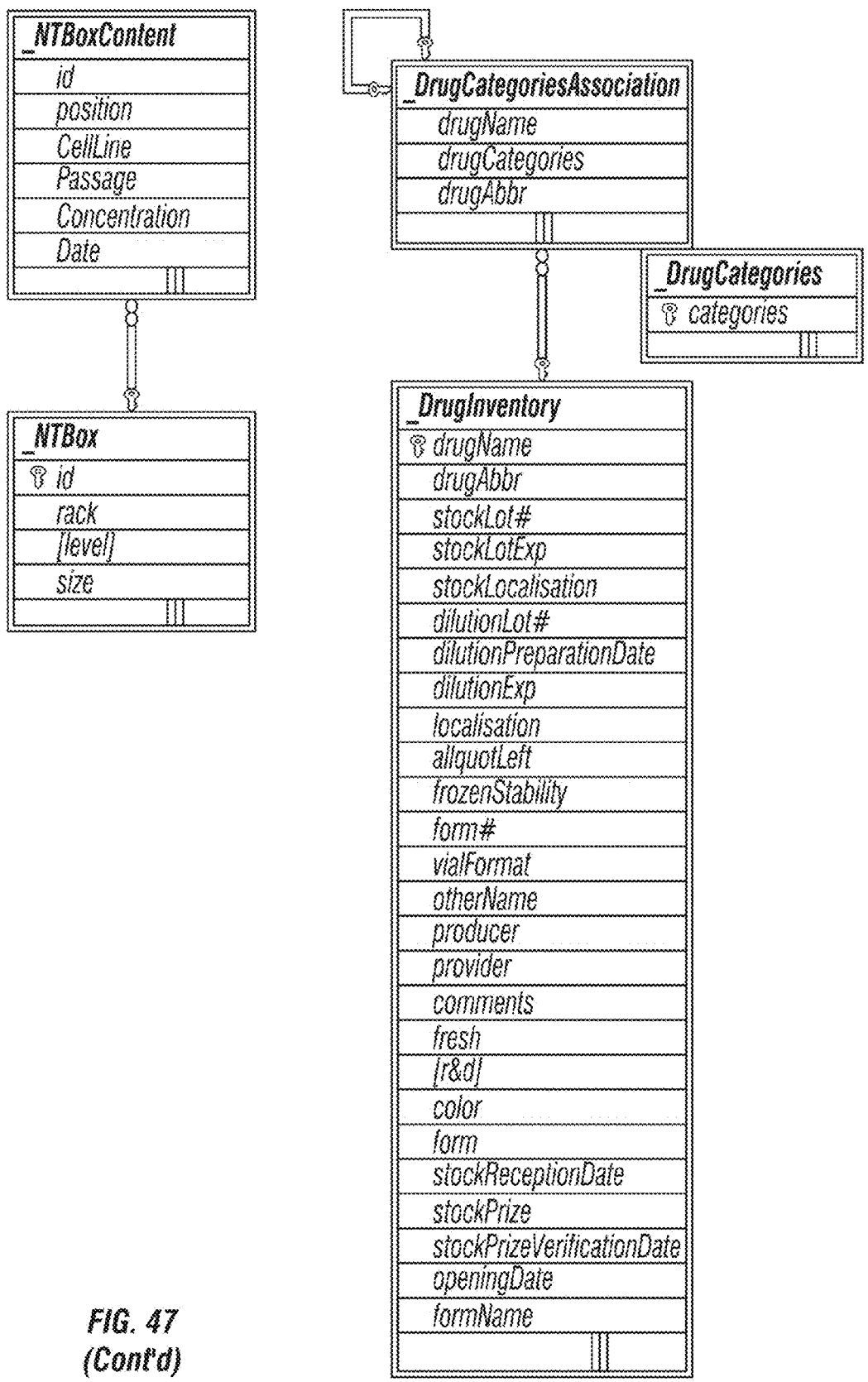
Figure 47:
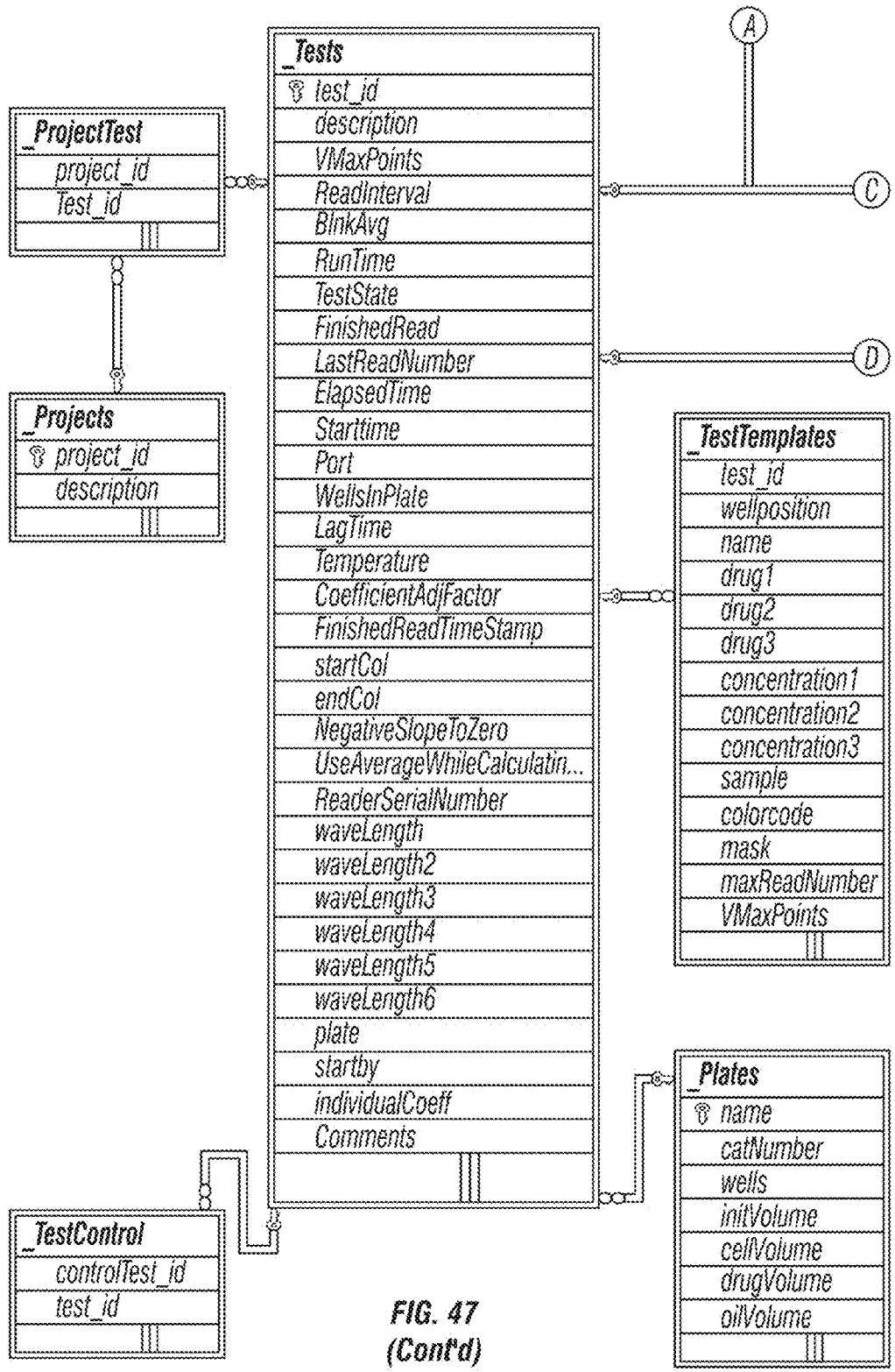
Figure 47:
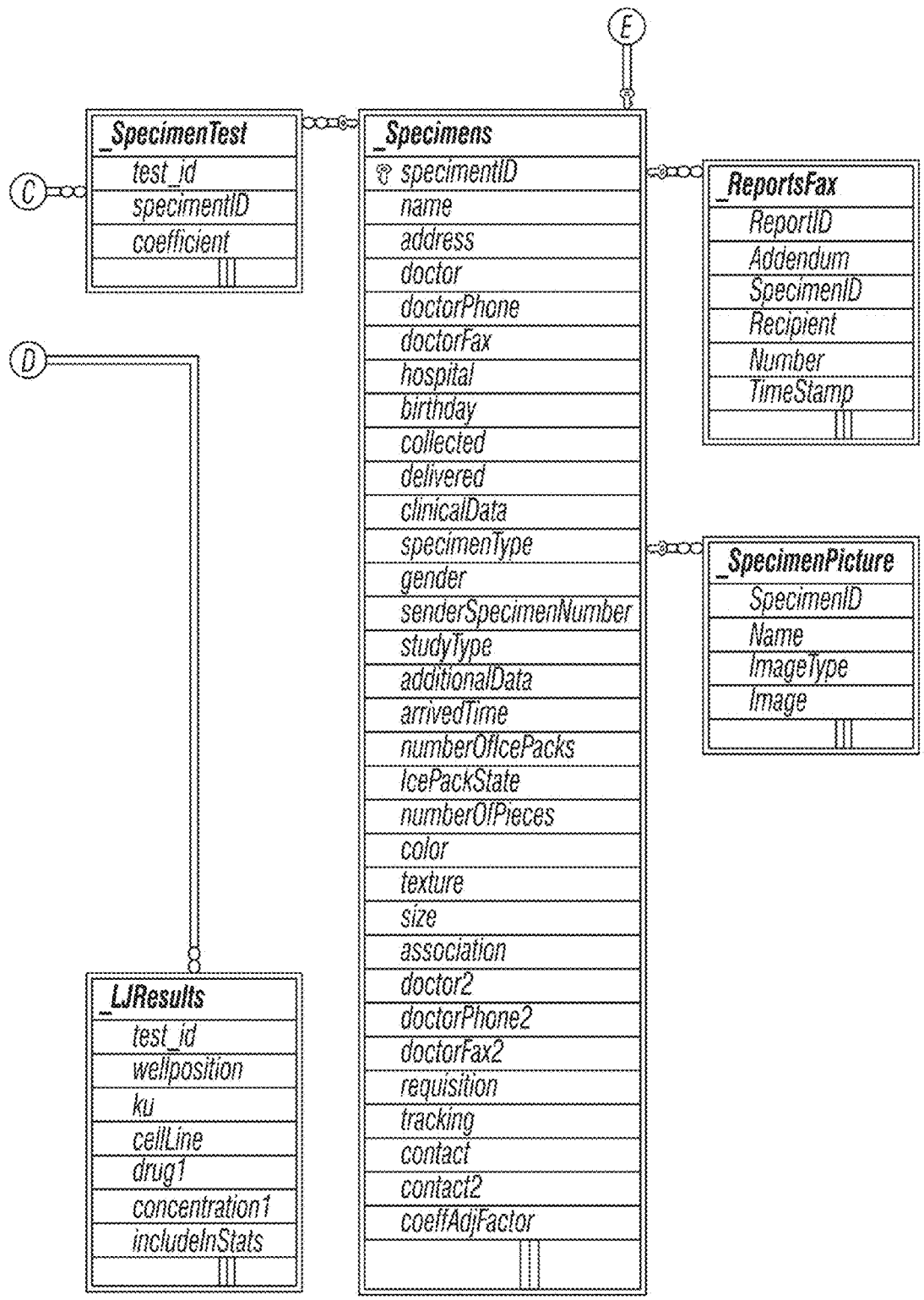

Finally, with respect to FIG. 47, a preferred embodiment of a relational database structure used in connection with the present invention is shown. Although these figures are provided sequentially due to space constraints, they can be arranged in a 3×3 grid so that the relationship and connection between the various components can be better appreciated. For example, the first three sheets of FIG. 47 (pages 40-42) would comprise the first row of the grid, the second three sheets of FIG. 47 (pages 43-45) would comprise the middle row of the grid, and the last two sheets of FIG. 47 (pages 46 and 47) would comprise the first two sections of the third row of the grid. As is common, key icons denote unique field names whose value or content remains the same throughout the other areas of the database.

Sample Reports

Appendices A, B, and C are typical sample reports generated by OPIE based on the tests described herein. Each of the sample reports provides clinical information on the patient and medical conditions. For comparison purposes, a table is provided indicating the drug candidates tested (in order of their possible effectiveness) on the live cells from the specimen, along with their respective maximum kinetic units (KU). The reports also include a comparative chart correlating cell apoptosis (KU) against various concentrations of the tested drug candidates. Comments are included which describe the results obtained from the tests, along with recommendations on the drug candidates which performed best under those conditions. For further comparative purposes, the reports also include a list of those drugs which are currently representative of best practices or standard of care for the specific cancer and its stages of progression.

Appendix A is a report based on tests conducted on a solid tumor specimen involving lung cancer metastases. The report indicates that paclitaxel a maximum 7.6 KU, followed by a combination of cisplatin and paclitaxel with 6.0 KU.

Appendix B is a report based on tests conducted on a blood specimen involving acute myeloid leukemia (AML). The report indicates that Cytoxan (cyclophosphamide) gave high effectiveness with 7.4 KU, even though Cytoxan is not a typical drug of choice for AML. When used in combination with daunorubicin, a higher value of 9.8 KU was achieved, suggesting that this combination would be more effective than Cytoxan alone.

Appendix C is a report based on tests conducted on an effusion specimen involving breast cancer. The combination of Cytoxan with doxorubicin and docetaxel indicates a sensitivity of 7.9 KU, suggesting that this combination is the recommended drug regimen for this patient.

All references cited in this specification are herein incorporated by reference as though each reference was specifically and individually indicated to be incorporated by reference. The citation of any reference is for its disclosure prior to the filing date and should not be construed as an admission that the present invention is not entitled to antedate such reference by virtue of prior invention.

It will be understood that each of the elements described above, or two or more together may also find a useful application in other types of methods differing from the type described above. Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention set forth in the appended claims. The foregoing embodiments are presented by way of example only; the scope of the present invention is to be limited only by the following claims.

The invention claimed is:

1. A system for determining the relative effectiveness of anti-cancer drugs for treating cancer in a patient, comprising:
   a processor, the processor being a hardware component of the system;
   a spectrophotometer in electronic communication with the processor;
   an electronic alarm system; and
   a memory in communication with the processor, the memory storing a plurality of instructions that when executed by the processor, execute the steps of:
   (a) providing an interface application, displayed on an electronic device, said interface application having selectable options including at least an option to manage drug testing parameters, said interface application further including a virtual well plate associated with a physical well plate of the spectrophotometer, the virtual well plate including rows and columns of virtual wells corresponding to rows and columns of physical wells in the physical well plate;
   (b) in response to a user selection, via an electronic input device, of the option to manage drug testing parameters, selecting desired drug testing parameters in relation to the virtual well plate, and storing the drug testing parameters in a database;
   (c) in response to a user selection, via an electronic input device, controlling the spectrophotometer to start a drug test, wherein the physical well plate includes at least one test well containing:
      (1) viable cancer cells harvested from the patient; and
      (2) at least one drug candidate in a predetermined concentration;
   and at least one control well containing the viable cancer cells alone;
   (d) recording the optical density of the test well at a predetermined wavelength at selected time intervals for a selected duration of time, and storing the optical density and time measurements in the database, wherein the electronic alarm system is operable to detect an anomaly in optical density data based, at least in part, on the optical density measurements stored in the database, and to send a notification to a designated recipient upon detection of the anomaly in the optical density data;
   (e) calculating an activity value based, at least in part, on the optical density measurements, time measurements and drug testing parameters corresponding to the test well and stored in the database, wherein the activity value corresponds to a change in the optical density measurements over time; and (f) providing information indicative of the activity value of the at least one drug candidate relative to activity values of other drug candidates tested the same way, thereby to show the relative effectiveness of the drug candidate for treating the cancer in the patient.

2. The system of claim 1, wherein the activity value is a kinetic units value calculated based on changes in the optical density measurements corresponding to the test well as a function of time.

3. The system of claim 1, wherein the interface application further includes at least one option to select drug testing projects.

4. The system of claim 1, wherein the interface application further includes at least one option to select administrative tasks associated with the drug tests.

5. The system of claim 1, wherein the database resides on a server accessed by one or more workstations.

6. The system of claim 5, wherein the server includes one or more services in communication with one or more spectrophotometers.

7. The system of claim 5, further including a remote power switch in communication with the server enabling remote power cycling of the spectrophotometer, a battery in operable communication with the remote power switch, and a generator capable of charging the battery.

8. The system of claim 1, wherein the interface application includes a least one option to generate one or more reports based on the drug candidate's ability to induce apoptosis in the cancer cells.

9. The system of claim 8, wherein the report includes comparative data between a plurality of drug candidates tested.

10. The system of claim 8, wherein the report includes a list of the drug candidates tested in order of their respective activity value.

11. The system of claim 8, wherein the report includes a comparative chart showing the activity value of the drug candidates tested against one or more concentrations of the drug candidates tested.

12. The system of claim 1, wherein the interface application further includes at least one option to select information corresponding to a cell line used in connection with the drug tests.

13. A method for determining the relative effectiveness of anti-cancer drugs for treating cancer in a patient, comprising:

performing, with a processor, the processor being a hardware component of a system:

(a) providing an interface application, displayed on an electronic device, said interface application having selectable options including at least an option to manage drug testing parameters, said interface application further including a virtual well plate associated with a physical well plate of a spectrophotometer, the virtual well plate including rows and columns of virtual wells corresponding to rows and columns of physical wells in the physical well plate;

(b) in response to a user selection, via an electronic input device, of the option to manage drug testing parameters, selecting desired drug testing parameters in relation to the virtual well plate, and storing the drug testing parameters in a database;

(c) in response to a user selection, via an electronic input device, controlling the spectrophotometer to start a drug test, wherein the physical well plate includes at least one test well containing:

(1) viable cancer cells harvested from the patient; and (2) at least one drug candidate in a predetermined concentration;

and at least one control well containing the viable cancer cells alone;

(d) recording the optical density of the test well at a predetermined wavelength at selected time intervals for a selected duration of time, and storing the optical density and time measurements in the database, wherein an electronic alarm system detects an anomaly in optical density data based, at least in part, on the optical density measurements stored in the database, and sends a notification to a designated recipient upon detection of the anomaly in the optical density data;

(e) calculating an activity value based, at least in part, on the optical density measurements, time measurements and drug testing parameters corresponding to the test well and stored in the database, wherein the activity value corresponds to a change in the optical density measurements over time; and (f) providing information indicative of the activity value of the at least one drug candidate relative to activity values of other drug candidates tested the same way, thereby to show the relative effectiveness of the drug candidate for treating the cancer in the patient.

14. The method of claim 13, wherein the activity value is a kinetic units value calculated based on changes in the optical density measurements corresponding to the test well as a function of time.

15. The method of claim 13, wherein the interface application further includes at least one option to select drug testing projects.

16. The method of claim 13, wherein the interface application further includes at least one option to select administrative tasks associated with the drug tests.

17. The method of claim 13, wherein the database resides on a server accessed by one or more workstations.

18. The method of claim 17, wherein the server includes one or more services in communication with one or more spectrophotometers.

19. The method of claim 17, wherein the server is in communication with a remote power switch enabling remote power cycling of the spectrophotometer, the remote power switch is in operable communication with a battery, and the battery is coupled to a generator capable of charging the battery.

20. The method of claim 13, wherein the interface application includes a least one option to generate one or more reports based on the drug candidate's ability to induce apoptosis in the cancer cells.

21. The method of claim 20, wherein the report includes comparative data between a plurality of drug candidates tested.

22. The method of claim 20, wherein the report includes a list of the drug candidates tested in order of their respective activity value.

23. The method of claim 20, wherein the report includes a comparative chart showing the activity value of the drug candidates tested against one or more concentrations of the drug candidates tested.

24. The method of claim 13, wherein the interface application further includes at least one option to select information corresponding to a cell line used in connection with the drug tests.

25. The system of claim 1, wherein the electronic alarm system is operable to detect the anomaly in the optical density data by determining, at predetermined time intervals, whether expected optical density measurements have been recorded in the database.

26. The system of claim 7, wherein the server is operable to detect non-occurrence of an expected event and to control the remote power switch to reboot the spectrophotometer upon detection of non-occurrence of the expected event.

27. The system of claim 26, wherein the expected event comprises recording of an optical density measurement in the database.

28. The method of claim 13, wherein detecting the anomaly in the optical density data comprises determining, at predetermined time intervals, whether expected optical density measurements have been recorded in the database.

29. The method of claim 19, further comprising: detecting non-occurrence of an expected event and controlling the remote power switch to reboot the spectrophotometer upon detection of non-occurrence of the expected event.

30. The method of claim 29, wherein the expected event comprises recording of an optical density measurement in the database.

* * * * *